(12) United States Patent
Duatti et al.

(10) Patent No.: US 6,270,745 B1
(45) Date of Patent: Aug. 7, 2001

(54) RADIOACTIVE TRANSITION METAL NITRIDE HETEROCOMPLEX

(75) Inventors: Adriano Duatti; Cristina Bolzati; Licia Uccelli, all of Ferrara; Fiorenzo Refosco, Vicenza; Francesco Tisato, Padua, all of (IT)

(73) Assignee: Nihon Medi-Physics Co., Ltd., Hyogo-Ken (JP)

( * ) Notice: Subject to any disclaimer, the term of this patent is extended or adjusted under 35 U.S.C. 154(b) by 0 days.

(21) Appl. No.: 09/331,237
(22) PCT Filed: Dec. 16, 1997
(86) PCT No.: PCT/JP97/04626
  § 371 Date: Jun. 17, 1999
  § 102(e) Date: Jun. 17, 1999
(87) PCT Pub. No.: WO98/27100
  PCT Pub. Date: Jun. 25, 1998

(30) Foreign Application Priority Data

Dec. 18, 1996 (JP) .................................................. 8-338553

(51) Int. Cl.$^7$ ................................. A61K 51/00; C07F 5/00
(52) U.S. Cl. ..................... 424/1.77; 424/1.65; 424/1.69; 424/1.73; 534/10; 534/14
(58) Field of Search ................................. 424/1.65, 1.69, 424/1.49, 1.73, 1.77; 534/10–14

(56) References Cited

U.S. PATENT DOCUMENTS

| | | | |
|---|---|---|---|
| 4,916,214 | * 4/1990 | Chiu et al. | 534/14 |
| 5,300,278 | 4/1994 | Pasqualini et al. | 534/14 |
| 5,399,339 | 3/1995 | Pasqualini et al. | 424/1.53 |
| 5,496,929 | 3/1996 | Pasqualini et al. | 534/10 |

FOREIGN PATENT DOCUMENTS

| | | | |
|---|---|---|---|
| 5-508842 | 12/1993 | (JP) | C07F/13/00 |
| 7-500816 | 1/1995 | (JP) | A61K/51/00 |
| 7-110869 | 11/1995 | (JP) | C07F/13/00 |

* cited by examiner

*Primary Examiner*—Michael G. Hartley
(74) *Attorney, Agent, or Firm*—Sughrue, Mion, Zinn, Macpeak & Seas, PLLC (57) ABSTRACT

The present invention provides a single radioactive transition metal nitride heterocomplex which permits labeling of a physiologically active substance such as a peptide, hormone or the like without impairing the activity of the substance. The radioactive transition metal nitride heterocomplex of the present invention is represented by the following formula (I):

$$(M{\equiv}N)XY \qquad (I)$$

wherein a radioactive transition metal M is radioactive technetium or radioactive rhenium, N is a nitrogen atom, X is a diphosphine compound or a diarsine compound, and Y is a bindentate ligand having a combination of electron-donating atoms.

33 Claims, 4 Drawing Sheets

RADIOACTIVE TRANSITION METAL NITRIDE HETEROCOMPLEX

CROSS-REFERENCE TO RELATED APPLICATIONS

This Application is a 371 of PCT/JP97/04626, filed Dec. 16, 1997.

TECHNICAL FIELD OF THE INVENTION

The present invention relates to a radioactive transition metal nitride heterocomplex, a radiopharmaceutical comprising said complex, and a process for producing said complex. More particularly, the present invention relates to a radioactive transition metal nitride heterocomplex comprising a nitride of radioactive technetium or radioactive rhenium and two different ligands coordinated therewith, a radiopharmaceutical for diagnostic imaging or therapy containing said complex as an active ingredient, and a process for their production.

BACKGROUND ART

Of radioactive transition metals used in radiopharmaceuticals, $^{99m}$Tc is a nuclide most often used in the field of radiopharmaceuticals for diagnostic imaging, and $^{186}$Re and $^{188}$Re are nuclides preferably used in the field of radiopharmaceuticals for therapy. Since these radioactive transition metals have different coordination numbers in different oxidized states and can form various complexes together with various ligands, they are used usually in the form of a complex. For example, as a process for producing the complex, there is a process of chelating ligands with Tc atom at first, and then attaching a physiologically active substance to the chelate, or a process of attaching a physiologically active substance to ligands at first, and then coordinating a Tc atom therewith. Whichever process is employed, it is usually difficult to carry out the above-mentioned attachment while maintaining the whole activity of the physiologically active substance. Such attachment is more difficult particularly in the case of a small compound.

There has recently been proposed a process comprising replacing a part of a physiologically active substance by a complex containing a metal ion, without impairing the activity of the substance (D. Y. Chi et al., J. Med. Chem. 1994, 37, 928–937). This process is advantageous in that a metal-containing block is accurately attached to the physiologically active substance, so that a structure very close to that of the original physiologically active substance can be maintained. However, no generally applicable process has yet been established.

Transition metal nitride complexes are excellent in stability to hydrolysis. Therefore, when a transition metal nitride complex is subjected to exchange reaction with any of various ligands having a useful physiological activity, when used in a pharmaceutical, the nitride group of the nitride complex can remain bonded strongly to the metal atom. Accordingly, transition metal nitride complexes having various substituents have been proposed. For example, WO 90/06137 discloses diethyl bisdithiocarbamate-Tc nitride complex, dimethyl bisdithiocarbamate-Tc nitride complex, di-n-propyl bisdithiocarbamate-Tc nitride complex, N-ethyl-N-(2-ethoxyethyl)bisdithiocarbamate-Tc nitride complex, etc.

In addition, WO 89/08657 discloses a process for producing a transition metal nitride complex which comprises reacting a phosphine-based ligand like a polyphosphine as a reducing agent for the transition metal with the transition metal oxide, then reacting a nitride of a metal or ammonium as a nitrogen source for nitride with the reaction product to convert it to the corresponding nitride, and then coordinating a physiologically active monoclonal antibody or the like with this nitride.

In these processes, the choice of the ligand having a physiological active group is so important that it determines properties of the resulting pharmaceutical. But, the metal nitride complex can have various numbers of coordination positions from mono-dentate to quadridentate and hence is formed in plural forms. Therefore, it has been difficult to obtain a single complex stoichiometrically having a specific physiologically active ligand.

DISCLOSURE OF INVENTION

When the radioactive metal is technetium or rhenium, oxidation number ranges between valency of +I and +VII. The oxidation number of nitride complex is generally the valency of +V, the metal atom thereof has five coordination positions and is expected to have a steric molecular configuration represented by the following formula (V) or formula (VI):

The geometry of the formula (V) is referred to as "square pyramidal geometry (sp geometry)", and the geometry of the formula (VI) as "trigonal bipyramidal geometry (tbp geometry)". In the above formulas, a, b, c, d, a', b', c' and d' are symbols affixed to coordination positions for convenience of explanation.

The sp geometry of the formula (V) is a square pyramidal geometry in which the coordination positions a, b, c and d form a square as a base and N is a vertex. It is considered that the tbp geometry of the formula (VI) is composed of the two trigonal pyramidal geometries which have a' and d' as the respective vertexes and have a triangle formed by b', c' and N on the same plane as a common base.

The present inventors earnestly investigated a combination of ligands capable of forming a complex of a single structure, among ligands which are likely to be coordinated with a transition metal nitride, for example, bidentate ligands, tridentate ligands and quadridentate ligands, and a process for forming such a complex, and consequently found that a single and stable transition metal nitride can be obtained by coordinating different two bidentate ligands unsymmetrically. Thus, the present invention has been accomplished.

The present invention is intended to provide a novel single radioactive transition metal nitride heterocomplex which permits labeling of physiologically active substances such as peptides, hormones, etc. without impairing their activity.

The present invention is a radioactive transition metal nitride heterocomplex comprising a radioactive transition metal nitride and two different ligands coordinated therewith which is represented by the following formula (I):

$$(M\equiv N)XY \tag{I}$$

wherein a radioactive transition metal M is radioactive technetium or radioactive rhenium, N is a nitrogen atom, X is a diphosphine compound or a diarsine compound, and Y is a bidentate ligand having a combination of two electron-donating atoms which are selected from the group consisting of O, S and N and may be either charged or not.

Another aspect of the present invention is a process for producing a radioactive transition metal nitride heterocomplex according to claim 1, which comprises a first step of reacting an oxide of a radioactive active transition metal M with either carbazic acid or its derivative, or hydrazine or its derivative, and a diphosphine compound or a diarsine compound in a solution in the presence or absence of a reducing agent, to obtain an intermediate of radioactive transition metal nitride; and a second step of reacting said intermediate with a bidentate ligand having a combination of two electron-donating atoms selected from the group consisting of O, S and N.

By the process for producing a novel radoactive transition metal nitride heterocomplex of the present invention, a single radioactive transition metal nitride heterocomplex can be obtained in high yield without producing an optical isomer, etc. Said complex is a novel complex composed of a core of a transition metal nitride, a diphosphine compound as a neutral bidentate ligand, and an electron-donating bidentate ligand, and the physiological activity of the electron-donating bidentate ligand itself or the molecular structure of a physiologically active species attached thereto is hardly impaired. Thus, the present invention has made it possible to obtain a radiopharmaceutical having a strictly controlled molecular structure.

BRIEF DESCRIPTION OF THE DRAWINGS

Me: methyl group
Et: ethyl group
HOBt: N-hydroxybenzotriazole
EDC: 1-(3-dimethylaminopropyl)-3-ethylcarbodiimide
TFA: trifluoroacetic acid
TIS: tri-isopropylsilane
BOC: tert-butoxycarbonyl
Trt: trityl group

BEST MODE FOR CARRYING OUT THE INVENTION

The radioactive transition metal nitride heterocomplex of the present invention comprises a core of a metal nitride having a M≡N bond and different two bidentate ligands X and Y coordinated with the core. The two ligands X and Y are chosen so as to be coordinated with the core of the metal nitride having a M≡N bond and form an unsymmetrical tbp geometry to stabilize the complex, without producing an optical isomer or a geometrical isomer in the coordination. In the tbp geometry of the formula (VI), there is suitably chosen a ligand which is coordinated at trans conformation in relation to the metal ion so as to form a bridge bond between the two positions a' and d' facing each other at the longest distance among the four coordination positions a', b', c' and d' of the metal nitride core. Such coordination at the two positions a' and d' permits coordination of another ligand at cis conformation selectively at the remaining two positions b' and c'. It is considered that the bonded states of such two ligands X and Y are schematically shown by the formula (VII):

(VII)

wherein A—A denotes the ligand Y, and B—B denotes the ligand X.

Such a ligand X includes diphosphine compounds and diarsine compounds and is preferably a diphosphine or diarsine compound containing atoms having an affinity for π electrons, such as phosphorus atom or arsenic atom at a symmetrical positions. Preferable examples thereof are bisphosphine compounds of the following formula (II) having two phosphorus atoms which are π electron acceptors and are bonded to each other at a suitable distance through a methylene group, an oxygen atom, a sulfur atom, a nitrogen atom, an ethylenedioxy group, etc. so as to be coordinated at trans conformation in relation to a Tc atom.

(II)

wherein each of $R^1$, $R^2$, $R^3$ and $R^4$, which may be the same or different, is one member selected from the group consisting of a hydrogen atom, an alkyl group, a substituted alkyl group, an aryl group and a substituted aryl group, $R^5$ is a methylene group, each of Z's is one member selected from the group consisting of oxygen atom, a sulfur atom, a methylene group, $NR^6$ (wherein N is a nitrogen atom and $R^6$ is a hydrogen atom, an alkyl group, a substituted alkyl group, an aryl group, a substituted aryl group, an amino group, an amino acid chain, a biologically active group or a $—C(=O)R^7$ group (wherein $R^7$ is a hydrogen atom, an alkyl group, a substituted alkyl group, an aryl group, a substituted aryl group, an amino group, an amino acid chain or a biologically active group)) and an ethylenedioxy group, P is a phosphorus atom, n is an integer in a range of $1 \leq n \leq 5$, and m is zero or 1. Preferably, n is an integer in a range of $2 \leq n \leq 4$.

Specifically, of the diphosphine compounds of 5 the above formula (II) wherein Z is $NR^6$, there are preferably used bisphosphine compounds represented by the following formula (III) or formula (IV) (hereinafter referred to as PNP type):

(III)

wherein Ph is a phenyl group and $R^6$ is a hydrogen atom, an alkyl group, a substituted alkyl group, an aryl group, a substituted aryl group, an amino group, an amino acid chain, a biologically active group or a $—C(=O)R^7$ group (wherein $R^7$ is a hydrogen atom, an alkyl group, a substituted alkyl group, an aryl group, a substituted aryl group, an amino group, an amino acid chain or a biologically active group).

(IV)

wherein X is an integer in a range of $0 \leq X \leq 4$, W is an integer in a range of $0 \leq W \leq 3$, and $R^6$ is a hydrogen atom, an alkyl group, a substituted alkyl group, an aryl group, a substituted aryl group, an amino group, an amino acid chain, a biologically active group or a $—C(=O)R^7$ group (wherein $R^7$ is a hydrogen atom, an alkyl group, a substituted alkyl group, an aryl group, a substituted aryl group, an amino group, an amino acid chain or a biologically active group).

As the diphosphine compounds of the formula (III), there can be exemplified bis(diphenylphosphinoethyl)amine $((C_6H_5)_2—P—CH_2CH_2—NH—CH_2CH_2—P—(C_6H_5)_2)$, bis(diphenylphosphinoethyl)methylamine $((C_6H_5)_2—P—CH_2CH_2—N(CH_3)—CH_2CH_2—P—(C_6H_5)_2)$, bis(diphenylphosphinoethyl)ethylamine $((C_6H_5)_2—P—CH_2CH_2—N(CH_2CH_3)—CH_2CH_2—P—(C_6H_5)_2)$, bis(diphenylphosphinoethyl)propylamine $((C_6H_5)_2—P—CH_2CH_2—N(CH_2CH_2CH_3)—CH_2CH_2—P—(C_6H_5)_2)$, bis(diphenylphosphinoethyl)butylamine $((C_6H_5)_2—P—CH_2CH_2—N(CH_2CH_2CH_2CH_3)—CH_2CH_2—P—(C_6H_5)_2)$, bis(diphenylphosphinoethyl)acetonylamine $((C_6H_5)_2—P—CH_2CH_2—N(CH_2COCH_3)—CH_2CH_2—P—(C_6H_5)_2)$ and bis(diphenylphosphinoethyl)methoxyethylamine $((C_6H_5)_2—P—CH_2CH_2—N(CH_2CH_2OCH_3)—CH_2CH_2—P—(C_6H_5)_2)$, etc.

As the diphosphine compounds of the formula (IV), there can be exemplified bis(dimethoxyphosphinoethyl)amine $((CH_3O)_2—P—CH_2CH_2—NH—CH_2CH_2—P—(OCH_3)_2)$, bis(dimethoxyphosphinoethyl)methylamine $((CH_3O)_2—P—CH_2CH_2—N(CH_3)—CH_2CH_2—P—(OCH_3)_2)$, bis(dimethoxyphosphinoethyl)ethylamine $((CH_3O)_2—P—CH_2CH_2—N(CH_2CH_3)—CH_2CH_2—P—(OCH_3)_2)$, bis(dimethoxyphosphinoethyl)propylamine $((CH_3O)_2—P—CH_2CH_2—N(CH_2CH_2CH_3)—CH_2CH_2—P—(OCH_3)_2)$, bis(dimethoxypropylphosphinoethyl)ethylamine $([CH_3O(CH_2)_3]_2—P—CH_2CH_2—N(CH_2CH_3)—CH_2CH_2—P—[(CH_2)_3OCH_3]_2)$, bis(dimethoxypropylphosphinoethyl)propylamine $([CH_3O(CH_2)_3]_2—P—CH_2CH_2—N(CH_2CH_2CH_3)—CH_2CH_2—P—[(CH_2)_3OCH_3]_2)$, bis(diethoxyethylphosphinoethyl)ethylamine $((CH_3CH_2OCH_2CH_2)_2—P—CH_2CH_2—N(CH_2CH_3)—CH_2CH_2—P—(CH_2CH_2OCH_2CH_3)_2)$, bis(diethoxyethylphosphinoethyl)propylamine $((CH_3CH_2OCH_2CH_2)_2—P—CH_2CH_2—N(CH_2CH_2CH_3)—CH_2CH_2—P—(CH_2CH_2OCH_2CH_3)_2)$, bis(dimethoxypropylphosphinoethyl)methoxyethylamine $([CH_3O(CH_2)_3]_2—P—CH_2CH_2—N(CH_2CH_2OCH_3)—CH_2CH_2—P—[(CH_2)_3OCH_3]_2)$ and bis(diethoxyethylphosphinoethyl)methoxyethylamine $((CH_3CH_2OCH_2CH_2)_2—P—CH_2CH_2—N(CH_2CH_2OCH_3)—CH_2CH_2—P—(CH_2CH_2OCH_2CH_3)_2)$, etc.

Of the diphosphine compounds of the above formula (II), wherein Z is an ethylenedioxy group (hereinafter referred to as POOP type), there can be exemplified, bis(diphenylphosphinoethyl)dioxyethylene $((C_6H_5)_2—P—CH_2CH_2—OCH_2CH_2O—CH_2CH_2—P—(C_6H_5)_2)$ or bis(dimethoxyphosphinoethyl)dioxyethylene $((CH_3O)_2—P—CH_2CH_2—OCH_2CH_2O—CH_2CH_2—P—(OCH_3)_2)$; wherein Z is an oxygen atom (hereinafter referred to as POP type), there can be exemplified bis(diphenylphosphinoethyl)ether $((C_6H_5)_2—P—CH_2CH_2—O—CH_2CH_2—P—(C_6H_5)_2)$; wherein Z is a sulfur atom (hereinafter referred to as PSP type), there can be exemplified bis(diphenylphosphinoethyl)sulfide $((C_6H_5)_2—P—CH_2CH_2—S—CH_2CH_2—P—(C_6H_5)_2)$; and wherein Z is a methylene group (hereinafter referred to as $P(CH_2)_nP$ type), there can be exemplified bis(diphenylphosphinoethyl)alkylene such as bis(diphenylphosphinoethyl)tetramethylene $((C_6H_5)_2—P—CH_2CH_2—(CH_2)_4—CH_2CH_2—P—(C_6H_5)_2)$, and bis(diphenylphosphinoethyl)pentamethylene $((C_6H_5)_2—P—CH_2CH_2—(CH_2)_5—CH_2CH_2—P—(C_6H_5)_2)$; etc.

In an intermediate formed by coordinating a diphosphine compound as the ligand X with an M≡N bond as described above, Cl$^-$, OH$^-$ or the like is coordinated at the remaining two coordination positions to form the tbp geometry, so that the intermediate is stabilized. The stabilized intermediate easily undergoes an exchange reaction with the bidentate ligand Y having an electron-donating atom pair, to form a useful radioactive transition metal nitride heterocomplex. When such an intermediate is formed, a complex having a single coordination geometry can be obtained without producing an optical isomer, etc., in the subsequent exchange reaction with the bidentate ligand having an electon-donating atom pair.

The bidentate ligand Y has a combination of two electron-donating atoms which are selected from the group consisting of O, S and N and may be either charged or not. As the aforesaid combination of electron-donating atoms, there can be exemplified [N$^-$, S$^-$], [O$^-$, S$^-$], [S$^-$, S$^-$], [N$^-$, S], [N, S$^-$], [O, S$^-$], [O, O$^-$], [O$^-$, N$^-$], [N$^-$, N$^-$], [O$^-$, S], [O$^-$, O$^-$], [O$^-$, N], [S, S$^-$], [N, N$^-$], [O, N$^-$], [O, N], [N, N], [S, S], [O, O], [N, S] and [O, S]. Preferable examples of the combination are [N$^-$, S$^-$], [O$^-$, S$^-$], [S$^-$, S$^-$], [N$^-$, S], [N, S$^-$], [O, S$^-$], [O, O$^-$], [O$^-$, N$^-$], [N$^-$, N$^-$], [O$^-$, S], [O$^-$, O$^-$], [O$^-$, N] and [S, S$^-$]. The bidentate ligand itself preferably comprises a physiologically active substance. As the physiologically active substance, there can be exemplified sugars, amino acids, fatty acids, hormones, peptides, and receptor-attachable ligands, etc. A bidentate ligand capable of forming various useful radioactive metal nitride heterocomplexes can be obtained by combining such a physiologically active substance with the above-exemplified combination of electron-donating atoms. For example, as compounds having a combination of electron-donating atoms [O$^-$, S$^-$], there can be exemplified 1-thio-β-D-glucose, thiosalicylic acid and their derivatives, etc. As compounds having a combination of electron-donating atoms [N$^-$, S$^-$], there can be exemplified cysteine, esters such as cysteine ethyl esters, peptides having a cysteine residue and 2-aminoethanethiol (H$_2$N—CH$_2$CH$_2$—SH), etc. As compounds having a combination of electron-donating atoms [S, S$^-$], there can be exemplified dithiocarbamic acid [H$_2$N—C(=S)—SH]; dithiocarbamic acid derivatives such as N-methyl-S-methyl dithiocarbamate [HN(CH$_3$)—C(=S)—SCH$_3$], N-diethyl dithiocarbamate [(C$_2$H$_5$)$_2$N—C(=S)—SH], N-ethyl dichiocarbamate [HN(C$_2$H$_5$)—C(=S)—SH] and N-ethoxy-N-ethyl dithiocarbamate [C$_2$H$_5$ON(C$_2$H$_5$)—C(=S)—SH], etc.; dithiocarbazic acid derivatives such as N-ethyl dithiocarbazate [H$_2$N—N(C$_2$H$_5$)—C(=S)—SH] and N-methyl-S-methyl dithiocarbazate, [H$_2$N—N(CH$_3$)—C(=S)—SCH$_3$], etc.; and [(cyclopentadienyl)(dithiocarbonylcyclopentadienyl)iron(II)] {Fe(C$_5$H$_5$)[C$_5$H$_4$C=S(SH)]}, etc. As compounds having a combination of electron-donating atoms [N,N], there can be exemplified ethylenediamine and phenylenediamine derivatives, etc. As compounds having a combination of electron-donating atoms [O,O], there can be exemplified salicylic acid, etc. As compounds having a combination of electron-donating atoms [O, N], there can be exemplified glucosamine, etc. Although these compounds themselves are physiologically active, other physiologically active substances such as sugars, amino acids, fatty acids, hormones, peptides, and receptor-attachable ligands may be bonded to the compounds.

The radioactive transition metal nitride heterocomplex of the present invention is produced by obtaining at first an intermediate [(M≡N)X]$_{int.}$ of the transition metal nitride complex having the tbp geometry or a pseudo-tbp geometry, from an oxide of a radioactive transition metal M and the above-exemplified diphosphine or diarsine compound X, and then reacting the intermediate with a bidentate ligand Y having the above-exemplified combination of electron-donating atoms.

In detail, the reactions are carried out as follows:

$$MO_4^- + X + D \rightarrow [(M\equiv N)X]_{int.} \quad (1)$$

$$[(M\equiv N)X]_{int.} + Y \rightarrow (M\equiv N)XY \quad (2)$$

wherein D is a nitrogen donor for forming the metal nitride. The nitrogen donor D is selected from the compounds having the >N—N< functional group. As a nitrogen donor D, there can be exemplified carbazic acid and carbazic acid derivatives such as N-methyl-S-methyl dithiocarbazate (H$_2$N—N(CH$_3$)—C(=S)SCH$_3$), N-methyl dithiocarbazate (H$_2$N—NH—C(=S)SCH$_3$), N-methyl-S-2-propionic acid dithiocarbazate (H$_2$N—N(CH$_3$)—C(=S)SCH(CH$_3$)COOH), etc.; hydrazine and hydrazine derivatives; hydrazide derivatives such as succinic acid dihydrazide, acetyl hydrazide, isonicotinic acid hydrazide; and sodium azide, etc. There are preferably used as a nitrogen donor D, N-methyl-S-methyl dithiocarbazate, succinic acid dihydrazide, acetyl hydrazide, isonicotinic acid hydrazide, sodium azide, etc. Although a single compound may be used as a nitrogen donor D, the yield of the intermediate can be increased by using different compounds as a nitrogen donor D simultaneously or successively. In the intermediate-producing reaction represented by the expression (1), a reducing agent such as tin(II) chloride, sodium dithionate or the like may be co-used. As the oxide of the transition metal M, there are used $^{99m}$TcO$_4^-$, $^{186}$ReO$_4^-$, $^{188}$ReO$_4^-$, etc.

Stricter control of the coordination of the physiologically active molecule with the transition metal nitride is very important for determining properties of the resulting radiopharmaceutical. In the above expression (1), when the pH of a reaction solution is in the acidic range, there is obtained a mixture of intermediates formed by the coordination of Cl$^-$, OH$^-$ or the like with the coordination position remaining after the coordination of a bisphosphine compound. Therefore, an intermediate having a single geometry can be obtained by adjusting the pH to 7 to 10 in the presence of a pH buffer solution, so that the exchange reaction can be more strictly controlled.

The intermediate-producing reaction is carried out at room temperature to 150° C. and at an acidic pH for 10 to 30 minutes.

The exchange reaction with the ligand represented by the above expression (2) is carried out by cooling the intermediate produced in the expression (1) to room temperature to 50° C., and then adding a buffer solution such as an HCO$_3^-$/CO$_3^{2-}$ buffer to adjust the pH to 7 to 10, preferably about 8. The buffer solution is not limited in kind so long as it can maintain the pH at 7 to 10. There are also used sodium phosphate buffers such as potassium dihydrogenphosphate/disodium hydrogenphosphate, potassium dihydrogenphosphate/sodium hydroxide, etc.

The stoichiometric ratio of the ligand X to the bidentate ligand Y, X/Y affects the yield of the radioactive metal nitride heterocomplex to be obtained. A suitable ratio of X to Y varies depending on the combination of X and Y. For example, when X is of a PNP type, the stoichiometric ratio X/Y is not particularly limited in the case where the bidentate ligand Y is N-methyl-S-methyl dithiocarbazate, aminoethanethiol, cysteine ethyl ester, 1-thio-β-D-glucose or thiosalicylic acid. However, in the case of using dimethyldithiocarbamate, N-diethyl dithiocarbamate, N-ethoxy-N-ethyl dithiocarbamate, when the ratio is in a range of X/Y<1, a complex having two molecules of the bidentate ligand Y as substituents, $^{99m}$Tc(N)(Y)$_2$ is produced as a by-product, resulting in a decreased yield of the objective asymmetrical radioactive metal nitride heterocomplex. Therefore, the conditions are preferably chosen so that the ratio may be in a range of X/Y≧1.

As another method for preventing the production of the complex having two molecules of ligand Y as substituents, $^{99m}$Tc(N)(Y)$_2$, there is thought of a method of increasing the steric hindrance of Y. For example, when [(cyclopentadienyl)(dithiocarbonylcyclopentadienyl)iron (II)] (hereinafter referred to as FcCS) is used as Y, a complex having two molecules of FcCS as substituents is hardly produced. When X/FcCS is 1, the proportion of $^{99m}$Tc(N)(FcCS)$_2$ produced is 5% or less. The reason can be speculated, for example, that the production of the complex having two molecules of FcCS as substituents is suppressed by the large steric hindrance of the bidentate ligard. The above fact suggests that a production of a complex having two molecules of ligand Y as substituents, $^{99m}$Tc(N)(Y)$_2$ is suppressed by the use of a bidentate ligand having large steric hindrance such as R(R')—N—C(=S)S$^-$ type, or R(R')—C—C(=S)S$^-$ type, or the like.

The transition metal nitride heterocomplex obtained by the reactions represented by the expression (1) and the expression (2) can be formulated into a radiopharmaceutical for diagnostic imaging or a radiopharmaceutical for therapy by its aseptic mixing thereof with pharmaceutically acceptable additives, for example, stabilizers such as ascorbic acid and p-aminobenzoic acid; pH adjusters such as sodium carbonate buffer and sodium phosphate buffer; solubilizers such as meglumine; and excipients such as D-mannitol. In addition, the radiopharmaceutical for diagnostic imaging or therapy according to the present invention can be provided in the form of a kit for preparation at the time of use which is obtained by combining the transition metal nitride heterocomplex with the above additives.

The radiopharmaceutical for diagnostic imaging and therapy according to the present invention can be administered by a conventional parenteral means such as intravenous administration, and the dosage thereof is determined depending on a radioactivity level at which imaging and treatment are considered possible, in view of the age and body weight of a patient, the condition of a disease to be cured, a radioactive imaging apparatus to be used, etc. When a radiopharmaceutical for diagnostic imaging obtained by using a $^{99m}$Tc-labeled substance is administered to a human being, the dosage thereof is 37 MBq to 1,850 MBq, preferably 185 MBq to 740 MBq, in terms of the radioactivity of $^{99m}$Tc.

The dosage of a radiopharmaceutical for therapy obtained by using a $^{186}$Re- or $^{188}$Re-labeled substance is 37 MBq to 18,500 MBq, preferably 370 MBq to 7,400 MBq, in terms of the radioactivity.

The radiopharmaceutical for diagnostic imaging and therapy according to the present invention had no acute toxicity so long as they were used in the dosage described above.

WORKING EXAMPLES

The present invention is illustrated below in further detail with examples, but the present invention is not limited to the examples.

The diphosphine compounds as ligands X and the bidentate ligands Y which are used in the following examples are abbreviated as follows:

Diphosphine compounds X:
PNP; $(C_6H_5)_2PCH_2CH_2N(C_2H_5)CH_2CH_2P(C_6H_5)_2$
PNP1; $(C_6H_5)_2CH_2CH_2PCH_2CH_2N(CH_2CH_2CH_3)CH_2CH_2PCH_2—CH_2(C_6H_5)_2$
PNP2; $(C_6H_5)_2PCH_2CH_2N(CH_2CH_2OCH_3)CH_2CH_2P(C_6H_5)_2$
PNP3; $[CH_3O(CH_2)_3]_2PCH_2CH_2N(CH_2CH_2OCH_3)CH_2CH_2P—[(CH_2)_3OCH_3]_2$
PNP4; $(C_6H_5)_2PCH_2CH_2N(CH_2CH_2CH_2CH_3)CH_2CH_2P(C_6H_5)_2$
PNP5; $(C_6H_5)_2PCH_2CH_2N(CH_2COCH_3)CH_2CH_2P(C_6H_5)_2$
POP; $(C_6R_5)_2PCH_2CH_2OCH_2CH_2P(C_6H_5)_2$
POOP; $(C_6H_5)_2PCH_2CH_2OCH_2CH_2OCH_2CH_2P(C_6H_5)_2$
PSP; $(C_6H_5)_2PCH_2CH_2SCH_2CH_2P(C_6H_5)_2$ Bidentate Ligands Y:
DTC; N-methyl-S-methyl dithiocarbazate
NS; aminoethanethiol
CysOEt; cysteine ethyl ester
tsa; thiosalicylic acid
DEDC; N-diethyl dithiocarbamate
NOEt; N-ethoxy-N-ethyl dithiocarbamate
β-glu; 1-thio-β-D-glucose
FcCS; [(cyclopentadienyl)(dithiocarbonylcyclopentadienyl)iron(II)]

EXAMPLE 1

Reaction for Producing an Intermediate

In a vial containing 5 mg of succinic acid dihydrazide (hereinafter abbreviated as SDH) were placed a solution obtained by dissolving 1.5 mg of bis(diphenylphosphinoethyl)ethylamine (PNP) in a mixture of 0.6 ml of ethanol and 0.1 ml (1.0 mol/l) of an aqueous hydrochloric acid solution, and then a physiologically acceptable $^{99m}$TcO$_4^-$ solution (0.5 ml, 50 MBq).

Figure 1:
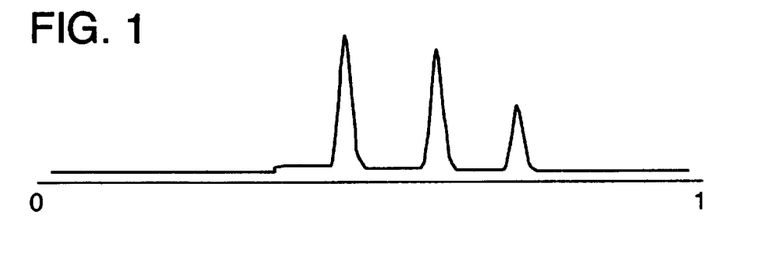
FIG. 1 is a chromatogram of a technetium-99m-nitride intermediate complex under acidic conditions.
Figure 2:
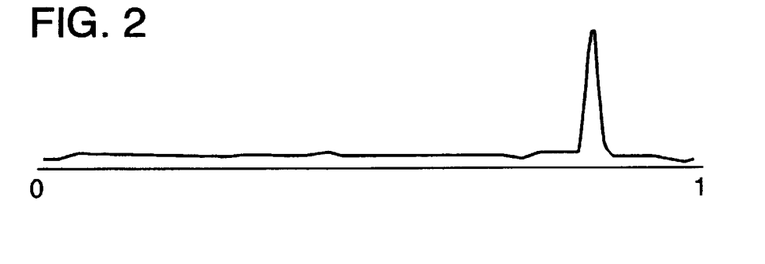
FIG. 2 is a a chromatogram of a technetium-99m-nitride intermediate complex under alkaline conditions.

The resulting mixture was heated at 80° C. for 20 minutes. The intermediate complex thus obtained was analyzed by high performance thin layer chromatography (HTLC) and high performance liquid chromatography (HPLC). FIG. 1 and FIG. 2 show radiochromatograms of the complex each of which was obtained by development on a silica gel plate with an ethanol/chloroform/benzene (0.85/2/1.5) mixture. Three peaks appeared in the chromatogram obtained under acidic conditions, indicating that three products were obtained (FIG. 1). On the other hand, when the pH was adjusted to about 8 or higher, a single peak appeared in the chromatogram (FIG. 2). From these facts, the following can be speculated: under the acidic conditions, the coordination positions remaining after the coordination of PNP are occupied by an unstable ligand such as Cl$^-$ or a water molecule; and when the pH is changed to about 8 or higher, such a ligand is replaced by an OH group, so that a single peak appears.

EXAMPLE 2

Reaction of 1-thio-β-D-glucose (β-glu) with the Intermediate

Figure 3:
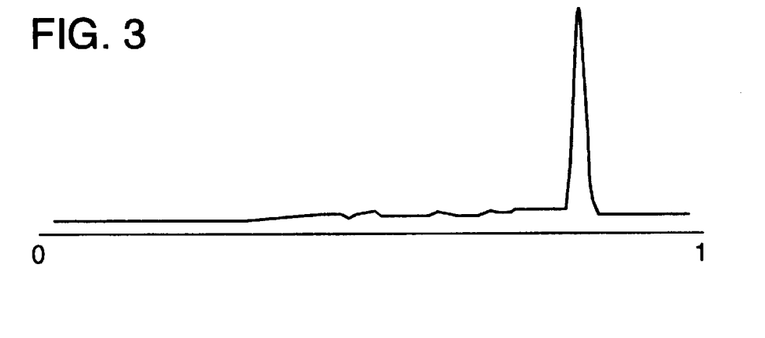
FIG. 3 is a chromatogram of a technetium-99m-nitride heterocomplex formed by coordination of bis(diphenylphosphinoethyl)ethylamine (PNP) and 1-thio-β-D-glucose (β-glu).

In a mixture of 0.6 ml of ethanol and 0.1 ml (1 mol/l) of an aqueous HCl solution were dissolved 5 mg of SDH and 1.5 mg of PNP, followed by adding thereto a physiologically acceptable $^{99m}$TcO$_4^-$ solution (0.5 ml, 50 MBq). The resulting mixture was heated at 80° C. for 20 minutes and then cooled to 40° C., after which 0.25 ml of HCO$_3^-$/CO$_3^{2-}$ buffer was added thereto to adjust the pH at about 8.0. Subsequently, a solution of 0.5 mg of β-glu in 1.5 ml of water was added. The complex finally obtained was analyzed by HTLC and HPLC. FIG. 3 shows a radiochromatogram of the complex which was obtained by development on a silica gel plate with tetrahydrofuran. The radiochemical purity of the final complex was higher than 95%. The complex contained a Tc≡N group in which a PNP bidentate ligand was coordinated with the metal ion at trans conformation and β-glu, i.e., another bidentate ligand containing a dianion was coordinated with the remaining two positions at cis conformation through the electronegative sulfur atom and the oxygen of a hydroxyl group which had lost a proton. The complex was stable.

EXAMPLE 3

Reaction of Thiosalicylic Acid (tsa) with the Intermediate

Figure 4:
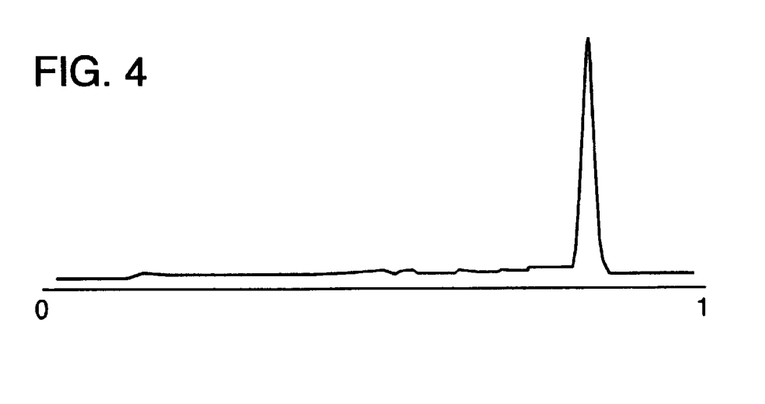
FIG. 4 is a chromatogram of a technetium-99m-nitride heterocomplex formed by coordination of PNP and thiosalicylic acid (tsa).

In a mixture of 0.6 ml of ethanol and 0.1 ml (1 mol/l) of an aqueous HCl solution were dissolved 5 mg of SDH and 1.5 mg of PNP, followed by adding thereto a physiologically acceptable $^{99m}$TcO$_4^-$ solution (0.5 ml, 50 MBq). The resulting mixture was heated at 80° C. for 20 minutes and then cooled to room temperature, after which 1 ml of sodium phosphate buffer (0.05 mol/l) was added thereto to adjust the pH to about 7.8. Subsequently, a solution of 5.0 mg of tsa in 0.20 ml of ethanol was added, and the resulting mixture was allowed to stand at room temperature for 5 minutes. The complex finally obtained was analyzed by HTLC and HPLC. FIG. 4 shows a radiochromatogram of the complex which was obtained by development on a silica gel plate with an ethanol/chloroform/benzene (0.7/2/1.5) mixture. The radiochemical purity of the final complex was higher than 95%. The complex contained a Tc≡N group in which a PNP bidentate ligand was coordinated with the metal ion at trans conformation and a dianion tsa as a bidentate ligand was coordinated with the remaining two positions through the electronegative sulfur atom which had lost a proton and the oxygen of the carboxyl group which had lost a proton. The solution of the complex was stable.

EXAMPLE 4

Reaction of N-ethoxy-N-ethyl dithiocarbamate (NOEt) with the Intermediate

Figure 5:
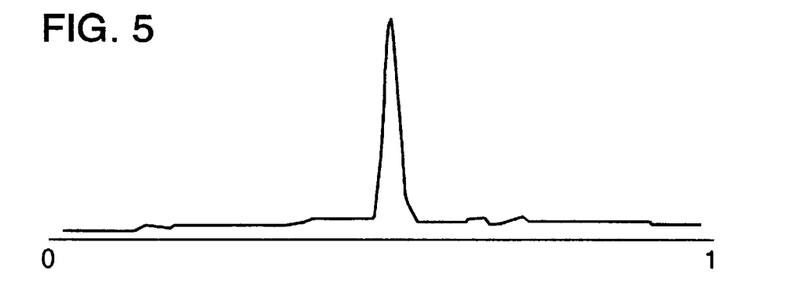
FIG. 5 is a chromatogram of a technetium-99m-nitride heterocomplex formed by coordination of PNP and N-ethoxy-N-ethyl dithiocarbamate (NOEt).

In a mixture of 0.6 ml of ethanol and 0.1 ml (1 mol/l) of an aqueous HCl solution were dissolved 5 mg of SDH and 1.5 mg of PNP, followed by adding thereto a physiologically acceptable $^{99m}TcO_4^-$ solution (0.5 ml, 50 MBq). The resulting mixture was heated at 80° C. for 20 minutes and then cooled to room temperature, after which 1 ml of sodium phosphate buffer (0.05 mol/l) was added thereto to adjust the pH to about 7.8. Subsequently, a solution of 5.0 mg of NOEt in 0.50 ml of water was added, and the resulting mixture was allowed to stand at room temperature for 5 minutes. The complex finally obtained was analyzed by HTLC and HPLC. FIG. 5 shows a radiochromatogram of the complex which was obtained by development on a silica gel plate with an ethanol/chloroform/benzene (1/2/1.5) mixture. The radio-chemical purity of the final complex was higher than 95%. The complex contained a Tc≡N group in which a PNP bidentate ligand was coordinated with the metal ion at trans conformation and a monoanion NOEt was coordinated with the remaining two positions through the two sulfur atoms of the $CS_2^-$ group. The solution of the complex was stable.

EXAMPLE 5

Figure 6:
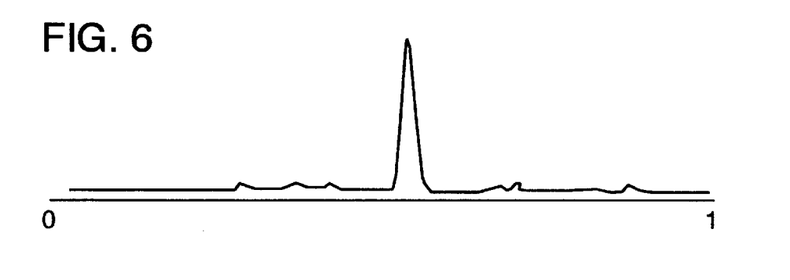
FIG. 6 is a chromatogram of a technetium-99m-nitride heterocomplex formed by coordination of PNP and cysteine (Cys).
Figure 7:
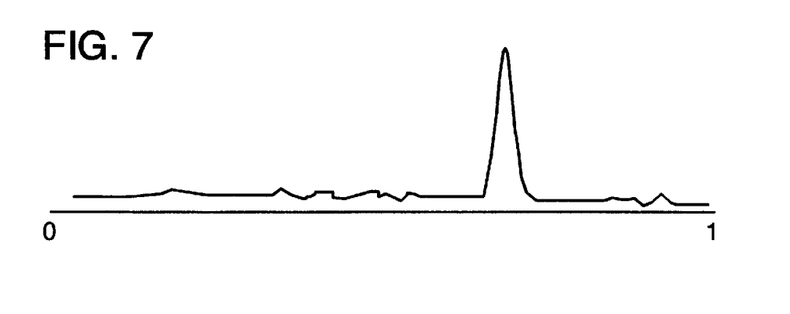
FIG. 7 is a chromatogram of a technetium-99m-nitride heterocomplex formed by coordination of PNP and cysteine ethyl ester (CysOEt).

Reaction of Each of Cysteine (Cys) and Cysteine Ester (CysOEt) with the Intermediate In a mixture of 0.6 ml of ethanol and 0.1 ml (1 mol/l) of an aqueous HCl solution were dissolved 5 mg of SDH and 1.5 mg of PNP, followed by adding thereto a physiologically acceptable $^{99m}TcO_4^-$ solution (0.5 ml, 50 MBq). The resulting mixture was heated at 80° C. for 20 minutes and then cooled to room temperature, after which 1 ml of sodium phosphate buffer (0.05 mol/l) was added thereto to adjust the pH to about 7.8. Subsequently, a solution of 3.0 mg of Cys in 0.50 ml of water was added, and the resulting mixture was allowed to stand at room temperature for 30 minutes. The complex finally obtained was analyzed by HTLC and HPLC. FIG. 6 shows a radiochromatogram of the complex which was obtained by development on a silica gel plate with an ethanol/chloroform/benzene (0.85/2/1.5) mixture. The radiochemical purity of the final complex was higher than 90%. The complex contained a Tc≡N group in which a PNP bidentate ligand was coordinated with the metal ion at trans conformation and a dianion Cys was coordinated with the remaining two positions through the sulfur atom which had lost a proton and the nitrogen atom of the amino group which had lost a proton. As a result of the same experiment as above except using an ester derivative (CysOEt), it was found that the carboxyl group of Cys did not participate in the coordination with the metal. CysOEt is formed by the replacement of the OH group of the carboxyl group of Cys by an ethoxy group, and the radiochemical purity of a final complex obtained from the ligand (CysOEt) was higher than 93% (FIG. 7). Solutions of the complexes, respectively, are all stable.

EXAMPLE 6

Reaction of a Tetrapeptide Cys-Lys-Pro-Val-NH$_2$ with the Intermediate

Figure 8:
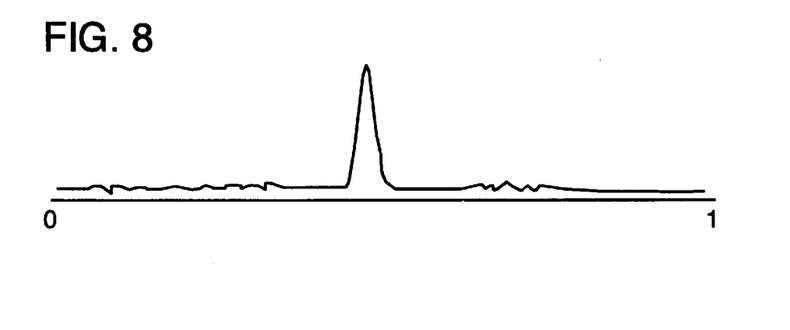
FIG. 8 is a chromatogram of a technetium-99m-nitride heterocomplex formed by coordination of PNP and Cys-Lys-Pro-Val-NH$_2$.

In a mixture of 0.6 ml of ethanol and 0.1 ml (1 mol/l) of an aqueous HCl solution were dissolved 5 mg of SDH and 1.5 mg of PNP, followed by adding thereto a physiologically acceptable $^{99m}TcO_4^-$ solution (0.5 ml, 50 MBq). The resulting mixture was heated at 80° C. for 20 minutes and then cooled to room temperature, after which 1 ml of sodium phosphate buffer (0.05 mol/l) was added thereto to adjust the pH to about 7.8. Subsequently, a solution of 1.0 mg of a tetrapeptide Cys-Lys-Pro-Val-NH$_2$ in 0.20 ml of water was added, and the resulting mixture was allowed to stand at room temperature for 30 minutes. The complex finally obtained was analyzed by HTLC and HPLC. FIG. 8 shows a radiochromatogram of the complex which was obtained by development on a reversed-phase C18 plate with a methanol/acetonitrile/tetrahydrofuran/ammonium acetate (3/3/2/2) mixture. The radiochemical purity of the final complex was higher than 90%. The complex contained a Tc≡N group in which a PNP bidentate ligand was coordinated with the metal ion at trans conformation and a dianionic tetrapeptide ligand was coordinated with the remaining two positions through the sulfur atom which had lost a proton and the nitrogen atom of the terminal cysteine residue which had lost a proton. The solution of the complex was stable.

EXAMPLE 7

Reaction for Producing an Intermediate

In the production of intermediates of metal nitride heterocomplexes represented by the formula (1), the influences of a nitrogen donor D and a diphosphine compound X were investigated by varying the kinds of D and X.

There were used $^{99m}Tc$ as a transition metal, DTC as the nitrogen donor D, and each of PNP1, PNP2, PNP4, PNP5, POP and POOP as the diphosphine compound X.

A solution of 1.0 mg of DTC and 3.0 mg of X (X=PNP1, PNP2, PNP4, PNP5, POP or POOP) dissolved in 1 ml of ethanol, 0.1 ml of an aqueous hydrochloric acid solution (1.0 mol/l) and 1.0 ml of $^{99m}TcO_4Na$ (approximately 400 MBq) were placed in a vial and kept at room temperature for 15 to 30 minutes.

When each of the resulting intermediates was subjected to thin layer chromatography (TLC: a silica gel plate), all of the intermediates obtained by varying the kind of the diphosphine compound X showed a single peak and their yields were 98% or more.

TLC (a silica gel plate) was carried out using the following mobile phase: ethanol/chloroform/benzene (1.5/2/1.5; Rf=0.53), or ethanol/chloroform/toluene/ammonium acetate (0.5 M) (5/3/3/1; Rf=0.68).

EXAMPLE 8

Reaction for Producing an Intermediate

In the same manner as in Example 7, a solution of 5.0 mg of SDH and 3.0 mg of X (X=PNP1, PNP2, PNP4, PNP5, POP or POOP) dissolved in 1 ml of ethanol, 0.1 ml of an aqueous hydrochloric acid solution (1.0 mol/l) and 1.0 ml of $^{99m}TcO_4Na$ (approximately 400 MBq) were placed in a vial and kept at room temperature for 15 to 30 minutes.

When each of the resulting intermediates was subjected to TLC (a silica gel plate), no residual pertechnetate was found but all the intermediates were mixtures. When 1.0 mg of DTC as a bidentate ligand Y was added to each of the mixtures at room temperature, the intermediate mixture was instantaneously converted to a single compound which showed a single peak. The yield of this compound was 98% or more. This compound exhibited the same HTLC pattern as that of the compound obtained in Example 7, which is indicated that the two compounds were identical. Thus, it is indicated that DTC is useful as a nitrogen donor D, at the same time that DTC is also useful as a bidentate ligand Y.

EXAMPLE 9

Reaction for Producing an Intermediate

In the same manner as in Example 7, a solution of 5.0 mg of DTCOOH (N-methyl-S-2-propionic acid dithiocarbazate) as nitrogen donor D and 3.0 mg of a diphosphine compound X (X=PNP1, PNP2, PNP4, PNP5, POP or POOP) dissolved in 0.1 ml of ethanol, 0.1 ml of an aqueous hydrochloric acid solution (1.0 mol/l) and 1.0 ml of $^{99m}TcO_4Na$ (approximately 400 MBq) were placed in a vial. After the vial was kept at room temperature for 15 to 30 minutes, the pH was adjusted to 10 by adding 0.25 mg of $NaHCO_3/Na_2CO_3$ (0.5 M).

Each of the resulting intermediates was subjected to TLC (a silica gel plate). All of the intermediates obtained by using the different diphosphine compounds X showed a single peak and their yields were 98% or more.

EXAMPLE 10

Reaction for Producing a Complex

For investigating the influences of a diphosphine compound x and a bidentate ligand Y on a reaction for producing an asymmetrical radioactive metal nitride heterocomplex, a reaction for producing an intermediate of the formula (I) was carried out and then the pH of the reaction solution was adjusted by adding a buffer solution ($NaH_2PO_4/Na_2HPO_4$, pH=7.4 or $NaHCO_3/Na_2CO_3$, pH=10), after which a suitable bidentate ligand Y was added and a vial containing them was kept at room temperature. The finally obtained complex $^{99m}Tc(N)(X)(Y)$ was monitored by a TLC.

SDH was used as a nitrogen donor D, each of PNP1, PNP2, PNP4 and PNP5 was used as the diphosphine compound X, and each of DTC, NS, CysOEt, tsa and β-glu, having a combination of electron-donating atoms [$NH^-$,S], [NH, $S^-$] or [$O^-$, $S^-$], was used as the bidentate ligand Y.

A solution of 5.0 mg of SDH and 3.0 mg of X (X= PNP1, PNP2, PNP4 or PNP5) dissolved in 1 ml of ethanol, 0.1 ml of an aqueous hydrochloric acid solution (1.0 mol/l) and 1.0 ml of $^{99m}TcO_4Na$ (approximately 400 MBq) were placed in a vial and the resulting mixture was kept at room temperature for 30 minutes. After the mixture was adjusted to pH 10 by adding 0.25 mg of $NaHCO_3/Na_2CO_3$ (0.5 M), 0.7 mg of NS was added thereto. A complex $^{99m}Tc(N)(X)(NS)$ was instantaneously formed, and its yield was 95% or more. Also when a bidentate ligand Y other than NS was used, a complex was instantaneously formed in the same yield as above.

When each of the complexes thus obtained was subjected to TLC (a silica gel plate), it showed a single peak. The TLC (a silica gel plate) was carried out using the following mobile phase: ethanol/chloroform/benzene (1.5/2/1.5; Rf=0.45), or ethanol/chloroform/toluene/ammonium acetate (0.5 M) (5/3/3/0.5; Rf=0.52).

EXAMPLE 11

Reaction for Producing a Complex

Using each of PNP1, PNP2, PNP4 and PNP5 as a diphosphine compound X and each of DEDC, NOEt and FcCS, having a combination of electron-donating atoms [$S^-$, S], as a bidentate ligand Y, their influences on the formation of a complex were investigated. A typical process is described below by taking the case where Y is DEDC.

A solution of 5.0 mg of SDH and 3.0 mg of X (X=PNP1, PNP2, PNP4 or PNP5) dissolved in 1 ml of ethanol, 0.1 ml of an aqueous hydrochloric acid solution (1.0 mol/l) and 1.0 ml of $^{99m}TcO_4Na$ (approximately 400 MBq) were placed in a vial and the resulting mixture was kept at room temperature for 30 minutes. After the mixture was adjusted to pH 10 by adding 0.25 mg of $NaHCO_3/Na_2CO_3$ (0.5 M), 0.2 mg of DEDC was added thereto. A complex $^{99m}Tc(N)(X)(DEDC)$ was instantaneously formed, and its yield was 90% or more.

When each of the complexes thus obtained was subjected to TLC (a silica gel plate), it showed a single peak. The TLC (a silica gel plate) was carried out using the following mobile phase: ethanol/chloroform/benzene (1.5/2/1.5; Rf=0.34), or ethanol/chloroform/toluene/ammonium acetate (0.5 M) (5/3/3/0.5; Rf=0.75).

In the case that DEDC or NOEt was used as bidentate ligand, when the amount of the bidentate ligand Y used was increased, the formation of an asymmetrical $^{99m}Tc$ nitride heterocomplex is accompanied by a $^{99m}Tc(N)(Y)_2$-producing reaction as side reaction, but the amount of $T^{99m}c(N)(Y)_2$ produced varied depending on the ratio of X to Y and was not dependent on the absolute amount of Y. That is, in the case of the bidentate ligands Y used in the present example, whichever diphosphine compound was used, the yield of the asymmetrical $^{99m}Tc$ nitride heterocomplex was high when the stoichiometrical ratio of the diphosphine compound X to the bidentate ligand Y, X/Y is in a range of X/Y≧1. In the case where X/Y<1, a compound having two molecules of the bidentate ligand as substituents, $^{99m}Tc(N)(Y)_2$ produced in a large amount, so that the production of the asymmetrical $^{99m}Tc$ nitride heterocomplex was decreased. When a bidentate ligand FcCS was used, $^{99m}Tc(N)(Y)_2$ was hardly produced. In the case where X/FcCS=1, the proportion of $^{99m}Tc(N)(Y)_2$ produced was 5% or less.

When DEDC was used as a bidentate ligand, the relation of the ratio of X/Y, the amount used for X and Y, and the yield of $^{99m}Tc(N)(PNP1)(DEDC)$ is shown below.

| X/Y | X(mg) | Y(mg) | Yield(%) |
|---|---|---|---|
| 15 | 3.0 | 0.2 | 90 |
| 10 | 10.0 | 1.0 | 78 |
| 10 | 5.0 | 0.5 | 76 |
| 10 | 3.0 | 0.3 | 81 |
| 1 | 10.0 | 10.0 | 46 |
| 1 | 5.0 | 5.0 | 50 |
| 1 | 3.0 | 3.0 | 52 |
| 0.3 | 3.0 | 10.0 | 26 |
| 0.1 | 1.0 | 10.0 | 20 |
| 0.1 | 0.5 | 5.0 | 21 |

EXAMPLE 12

Reaction for Producing a Complex

Using POP as a diphosphine compound X and each of DTC, DEDC, NOEt, tsa, FcCS, 62-glu, CysOEt and NS, having [NH⁻, S], [NH⁻, S⁻], [O⁻, S⁻] or [S, S⁻], as a bidentate ligand Y, their influences on the formation of a complex were investigated by synthesizing a complex $^{99M}$Tc(N)(X)(Y) in the same manner as in Example 10.

When Y is DTC, a $^{99m}$Tc nitride heterocomplex $^{99m}$Tc(N)(POP)(DTC)⁺ was obtained with a radiochemical purity of 95% or more. However, when DEDC, NOEt, tsa, FCCS, β-glu, CysOEt or NS was used as a bidentate ligand Y, the formation of the heterocomplex was always accompanied by the formation of $^{99m}$Tc(N)(Y)₂ having two molecules of Y as substituents. The extent of formation of the complex having two molecules of Y as substituents increased in the order DEDC>NOEt>tsa>FcCS>β-glu>CysOEt>NS.

EXAMPLE 13

Reaction for Producing a Complex

Using POOP as a diphosphine compound X and each of DTC, DEDC, NOEt, tsa, FcCS, β-glu, CysOEt and NS, having [NH⁻, S], [NH⁻, S⁻], [O⁻, S⁻] or [S, S⁻], as a bidentate ligand Y, their influences on the formation of a complex were investigated by synthesizing a complex $^{99m}$Tc(N)(X)(Y) in the same manner as in Example 10.

When POOP was used, a $^{99m}$Tc nitride heterocomplex $^{99m}$Tc(N)(POOP)(Y)$^{0/+}$ was obtained without production of a complex having two molecules of Y as substituents, whichever bidentate ligand was used.

EXAMPLE 14

Biodistribution

The biodistribution of a $^{99m}$Tc nitride heterocomplex represented by the general formula $^{99m}$Tc(N)(X)(Y) was investigated as follows: $^{99m}$Tc nitride heterocomplexes were synthesized using DTC as a bidentate ligand Y and each of the diphosphine compounds X described below, and the biodistribution in rats of each heterocomplex was investigated.

The $^{99m}$Tc nitride heterocomplexes of $^{99m}$Tc(N)(X)(DTC)$^{30}$ type were synthesized using each of the following diphosphine compounds POP, PNP1, PNP2 and PNP3:
POP; (C₆H₅)₂PCH₂CH₂OCH₂CH₂P(C₆H₅)₂
PNP1; (C₆H₅)₂PCH₂CH₂N(CH₂CH₂CH₃)CH₂CH₂P(C₆H₅)₂
PNP2; (C₆H₅)₂PCH₂CH₂N(CH₂CH₂OCH₃)CH₂CH₂P(C₆H₅)₂
PNP3; [CH₃O(CH₂)₃]₂PCH₂CH₂N(CH₂CH₂OCH₃)CH₂CH₂P—[(CH₂)₃OCH₃]₂
Production of $^{99m}$Tc Nitride Heterocomplexes $^{99m}$Tc(N)(X)(DTC)⁺

In a vial containing 1.0 mg of DTC, a solution of 0.1 mg of SnCl₂ in 0.1 ml of water, 1.0 ml of ethanol and 3.0 mg of X (X=POP, PNP1, PNP2 or PNP3) was placed 0.25 ml of $^{99m}$TcO₄⁻ (100 to 500 MBq), and the vial was allowed to stand at room temperature for 30 minutes or at 80° C. for 15 minutes. The yield of the complex was 90% or more. The thus obtained complexes were identified by a reversed-phase chromatography under the following conditions; column used: PRP-1 Hamilton column, mobile phase: [NH₄][CH₃COO] (0.1 M)/CH₃CN (containing 0.1% THF)=90/10, flow rate: 0.5 ml/min.
Measurement of Biodistribution Before being injected into rats, the contents of the vial were diluted with phosphate buffer (0.1 mol/dm³, pH=7.06) containing 10% Tween 80 (polyoxyethylenesorbitane monostearate). The complexes were stable in the solutions and in human plasma for at least 6 hours.

The biodistribution was measured using male Spraque-Dawley rats (SD rats) weighing 200 to 250 g. After 24 hours fasting, the rats were put under intraperitoneal anesthesia and given an injection in the jugular vein. Then, the organs were excised from the rats at different intervals of time, washed and then weighed. In addition, blood samples were collected and then weighed. The data on the biodistribution are expressed as the mean±significant difference of the percentage of radioactivity level per gram of the organ weight based on the dose of radioactivity, (% dose/g). The measurement was carried out using groups of 5 rats each. The measurement results are shown in Tables 1 to 4.

Since the structures of the heterocomplexes used in the experiment are the same except for the different portion derived from the diphosphine compound, it can be speculated that the difference of the biodistribution reflects the difference of the diphosphine compound. The diphosphine compounds used in the experiment can be represented by the formula R₂P—CH₂CH₂—Z—CH₂CH₂—PR₂ in which two groups R are bonded to each phosphorus atom and a crosslinking group Z is bonded to two ethylene groups. When R is a phenyl group and the group Z is each of various groups Z=O, >N—CH₂CH₂CH₃ and >N—CH₂CH₂OCH₃, the biodistribution of all the complexes did not exhibit any significant accumulation of the complexes in brain and heart. The complexes were relatively rapidly washed out from lung and blood, and the complexes were eliminated through the liver and the kidney.

A complex $^{99m}$Tc(N)(PNP3)(DTC)⁺ obtained by replacing R by —CH₂CH₂CH₂OCH₃ and using >N—CH₂CH₂OCH₃ as Z was accumulated particularly in heart in a very large amount which was substantially constant throughout the measurement. This complex was rapidly washed out from lung and blood, and was relatively rapidly eliminated from kidney and liver. Thus, it is indicated that the complex is easily metabolized. Such marked accumulation in heart suggests that $^{99m}$Tc(N)(PNP3)(DTC)⁺ or its derivative can be used as a radiopharmaceutical diagnostic imaging for blood flow in myocardium.

EXAMPLE 15

Figure 9:
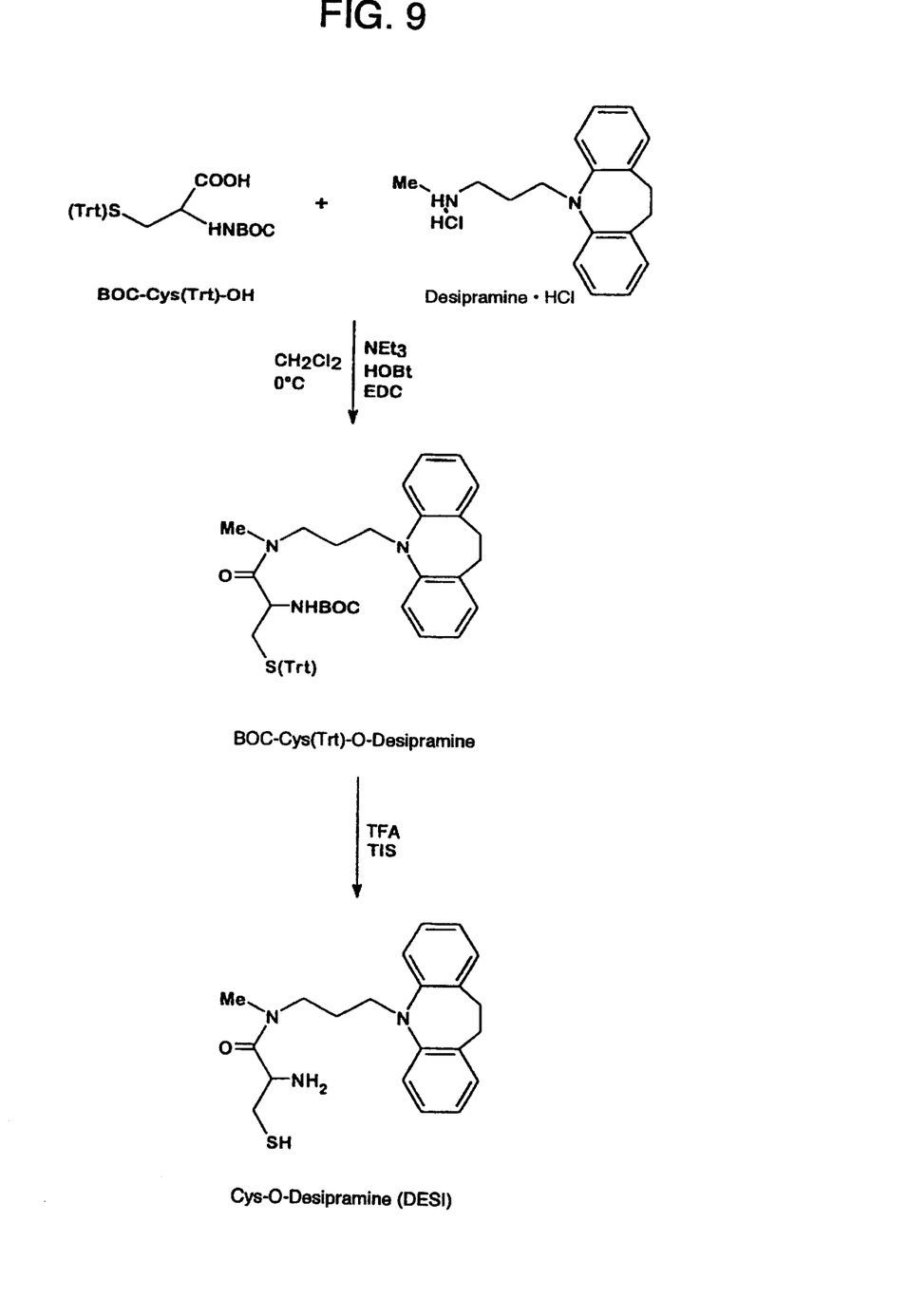
FIG. 9 is a synthesis scheme of cysteine-desipramine (DESI). The abbreviations in the figure indicate the substituents or compounds as follows.

Synthesis of a Bidentate Ligand Cysteine-desipramine and a $^{99m}$Tc Nitride Hetero-Complex Thereof Synthesis of Cysteine-desipramine According to the synthesis scheme shown in FIG. 9, cysteine-desipramine (hereinafter abbreviated as DESI) was syntesized by bonding cysteine to desipramine, a derivative of imipramine which is a physiologically active substance having antidepressant effect.

The bidentate ligand DESI is formed by amide linkage between the carboxyl group of cysteine and the terminal nitrogen atom of desipramine.
Synthesis of a Complex Using PNP3 as a diphosphine compound X and DESI as a bidentate ligand Y, a $^{99m}$Tc nitride hetero-complex (hereinafter abbreviated as $^{99m}$TcN-DESI) was synthesized as follows.

(1) In a vial containing a suspension of 5 mg of SDH and 0.1 mg of SnCl₂ in 0.1 ml of physiological saline was placed 0.250 ml of $^{99m}$TcO₄Na (50.0 MBq to 3.0 GBq) and then 1.0 ml of ethanol, and the vial was allowed to stand at room temperature for 15 minutes. Subsequently, to the resulting solution were added a solution of 3.0 mg of PNP3 in 0.1 ml of ethanol and a solution of 5.0 mg of DESI in 0.1 ml of water, and the vial was heated at 100° C. for 15 minutes. The radiochemical purity of the thus obtained complex was 95% or more.

(2) The same complex as in (1) was synthesized by a one-stage process comprising placing $^{99m}TcO_4Na$, SDH, $SnCl_2$, PNP3 and DESI in the same vial in the following manner. In a vial containing 1.0 ml of ethanol and 0.5 ml of physiological saline were placed 5 mg of SDH, 0.1 mg of $SnCl_2$, 33.0 mg of PNP and 5 mg of DESI, and then 0.250 ml of $^{99m}TcO_4Na$ (50.0 MBq to 3.0 GBq). The vial was heated at 100° C. for 30 minutes. The radiochemical purity of the thus obtained complex was 90% or more.

Analysis

The obtained $^{99m}TcN$-DESI complex was identified by thin lager chromatography (TLC), high performance liquid chromatography (HPLC), electrophoresis and ion exchange chromatography. The measurement conditions are as follows.

TLC

Silica gel plate; mobile phase: ethanol/chloroform/benzene (1.5/2/1.5), Rf=0.19. Reversed phase (C18 plate); mobile phase: methanol/acetonitrile/tetrahydrofuran/ammonium acetate (0.5 mol/cc), Rf=0.31.

HPLC

Carried out with a high performance liquid chromatography apparatus manufactured by Beckman. Reversed phase (C18 plate); elution: 1 ml/min, (A) triethylamine ($NEt_3$) 0.1 M, pH=3 (containing 1 M $H_3PO_4$), (B) acetonitrile. The retention time of the complex was 25 minutes, while that of the ligand not made into the complex was 7 minutes.

Electrophoresis

Carried out by the use of Watman paper and phosphate buffer (0.1 M) at a voltage ($\Delta V$) of 150 V for 1.5 hours. There was not observed any electrophoretic migration indicating that the complex was neutral.

Ion Exchange Chromatography

Cation exchange resin: Sep-Pak CM (COONa), Millpore, anion exchange resin: Sep-Pak QMA ($CONH(CH_2)_3 N(CH_3)_3^+Cl$), Millpore, reversed phase column: Sep-Pak C18, Millpore. The complex was retained in an amount of about 95% in the cation exchange resin, about 60% in the anion exchange resin, or 99.5% in the reversed phase column. The high retention rate in the reversed phase column suggests that the complex is high lipophilic.

Structure of $^{99m}TcN$-DESI

Figure 10:
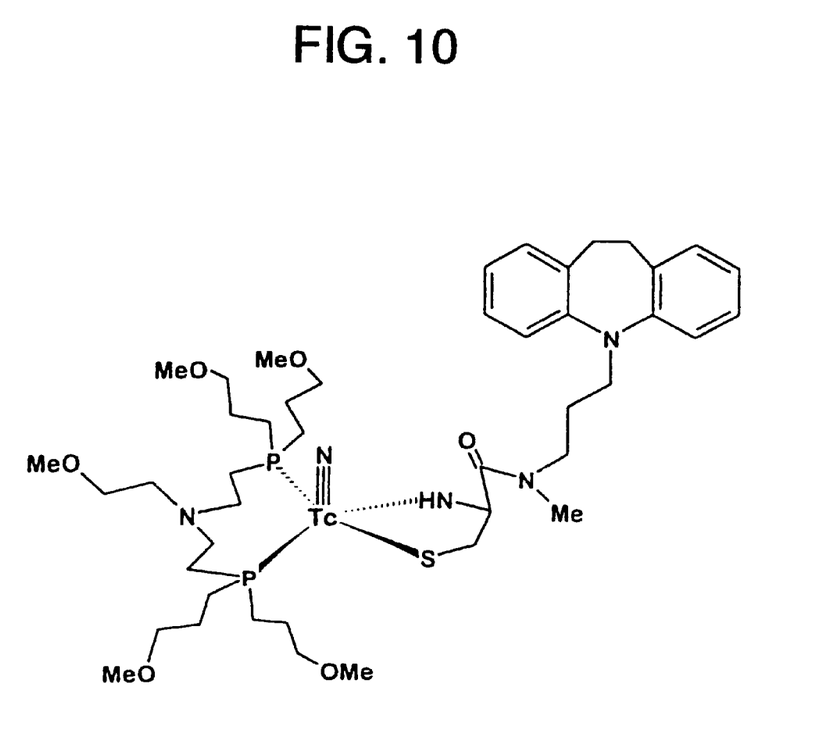
FIG. 10 is a structure of a technetium-99m-nitride heterocomplex formed by coordination of bis(dimethoxypropylphosphinoethyl)methoxyethylamine (PNP3) and cysteine-desipramine (DESI).

From the above experiments, it was conjectured that the structure of $^{99m}TcN$-DESI is as shown in FIG. 10.

EXAMPLE 16

Biodistribution of $^{99m}TcN$-DESI

The biodistribution of the $^{99m}TcN$-DESI in SD rats obtained in Example 15 was measured.

Before being injected into the rats, the $^{99m}TcN$-DESI was separated and purified from the excess and free bidentate ligand by HPLC. The active ingredient of the complex was further purified by passage through a Sep-Pak cartridge activated with 5 ml of 95% ethanol. The final active ingredient was recovered with 95% ethanol and diluted with physiological saline containing 10% Tween 80.

The rats were divided into two groups, group A and group B. Into each rat in group A was injected 20 $\mu$Ci of the $^{99m}TcN$-DESI. Into each rat in group B were injected 20 $\mu$Ci of the $^{99m}TcN$-DESI and 1.0 mg/kg of unlabeled desipramine at the same time.

SD rats weighing about 250 g were put under intraperitoneal anesthesia with a mixture of xylazine (18 mg/kg) and ketamine (15 mg/kg) and given an injection in the jugular vein. Then, the organs (brain, heart, lung, liver, spleen, kidney, muscle, adrenal, and submaxillary gland) were excised from the rats at different intervals of time, washed and then weighed. In addition, blood samples were collected and then weighed. The data on the biodistribution are expressed as the mean±significant difference of the percentage of radioactivity level per gram of the organ weight based on the dose of radioactivity, (% dose/g). The measurement was carried out using groups of 3 rats each. The measurement results are shown in Tables 5 to 8.

The $^{99m}TcN$-DESI complex was accumulated in heart in a considerable amount and in adrenal in a very large amount. The complex was very rapidly eliminated through liver and kidney. As shown in Tables 7 and 8, as to the biodistribution of the $^{99m}TcN$-DESI complex in brain, the complex was accumulated in cortex in a very small amount in group B to which unlabeled desipramine had been administered, but it was specifically accumulated in cortex in group A to which no unlabeled desipramine had been administered. Thus, it is suggested that the complex retained specificity for serotonin receptor.

TABLE 1

Biodistribution of $^{99m}Tc(N)(POP)(DTC)^+$ in Rats

| Time | Blood % dose/g | Brain % dose/g | Heart % dose/g | Lung % dose/g | Liver % dose/g | Spleen % dose/g |
|---|---|---|---|---|---|---|
| 0 min | 2.617 ± 0.04 | 0.142 ± 0.14 | 0.923 ± 0.04 | 2.792 ± 0.18 | 3.662 ± 0.43 | 2.202 ± 0.07 |
| 2 min | 1.254 ± 0.19 | 0.073 ± 0.00 | 0.73 ± 0.07 | 2.387 ± 0.08 | 4.821 ± 0.71 | 3.587 ± 0.99 |
| 10 min | 0.542 ± 0.02 | 0.029 ± 0.00 | 0.434 ± 0.05 | 1.19 ± 0.40 | 6.161 ± 0.47 | 3.538 ± 0.70 |
| 30 min | 0.547 ± 0.01 | 0.023 ± 0.00 | 0.428 ± 0.05 | 1.05 ± 0.13 | 6.199 ± 0.15 | 2.07 ± 0.55 |
| 1 hr | 0.261 ± 0.14 | 0.019 ± 0.00 | 0.42 ± 0.05 | 0.771 ± 0.09 | 5.128 ± 0.15 | 3.542 ± 1.23 |
| 2 hr | 0.145 ± 0.01 | 0.018 ± 0.01 | 0.384 ± 0.00 | 0.757 ± 0.05 | 3.05 ± 0.07 | 4.32 ± 0.19 |
| 4 hr | 0.125 ± 0.00 | 0.01 ± 0.00 | 0.303 ± 0.01 | 0.549 ± 0.03 | 1.538 ± 0.01 | 3.094 ± 0.50 |

| Time | Stomach % dose/g | Kidney % dose/g | Muscle % dose/g | Intestine % dose/g | Bone % dose/g |
|---|---|---|---|---|---|
| 0 min | 0.522 ± 0.09 | 3.141 ± 0.35 | 0.087 ± 0.00 | 0.482 ± 0.02 | 0.225 ± 0.01 |
| 2 min | 0.493 ± 0.02 | 5.952 ± 0.74 | 0.075 ± 0.00 | 0.581 ± 0.06 | 0.214 ± 0.05 |
| 10 min | 0.653 ± 0.06 | 4.805 ± 0.51 | 0.069 ± 0.01 | 0.934 ± 0.03 | 0.306 ± 0.07 |
| 30 min | 0.216 ± 0.01 | 3.25 ± 1.12 | 0.083 ± 0.03 | 0.64 ± 0.00 | 0.21 ± 0.02 |

TABLE 1-continued

Biodistribution of $^{99m}$Tc(N)(POP)(DTC)$^+$ in Rats

| | | | | | | |
|---|---|---|---|---|---|---|
| 1 hr | 0.944 ± 0.16 | 5.054 ± 0.18 | 0.068 ± 0.01 | 1.236 ± 0.03 | 0.327 ± 0.02 |
| 2 hr | 1.857 ± 0.22 | 5.145 ± 0.11 | 0.066 ± 0.03 | 1.478 ± 0.09 | 0.296 ± 0.01 |
| 4 hr | 1.74 ± 0.01 | 1.745 ± 0.11 | 0.067 ± 0.00 | 1.843 ± 0.02 | 0.321 ± 0.01 |

TABLE 2

Biodistribution of $^{99m}$Tc(N)(PNP1)(DTC)$^+$ in Rats

| Time | Blood % dose/g | Brain % dose/g | Heart % dose/g | Lung % dose/g | Liver % dose/g | Spleen % dose/g |
|---|---|---|---|---|---|---|
| 0 min | 2.125 ± 0.3 | 0.143 ± 0.02 | 1.236 ± 0.08 | 5.815 ± 0.04 | 3.593 ± 0.42 | 1.948 ± 0.20 |
| 2 min | 1.062 ± 0.13 | 0.086 ± 0.00 | 0.824 ± 0.01 | 4.653 ± 0.65 | 5.555 ± 0.83 | 4.459 ± 0.09 |
| 10 min | 0.495 ± 0.01 | 0.041 ± 0.00 | 0.795 ± 0.06 | 3.191 ± 0.60 | 5.795 ± 0.03 | 7.237 ± 0.88 |
| 30 min | 0.285 ± 0.01 | 0.027 ± 0.00 | 0.513 ± 0.07 | 2.089 ± 0.16 | 5.976 ± 0.49 | 5.884 ± 2.7 |
| 1 hr | 0.311 ± 0.03 | 0.019 ± 0.00 | 0.55 ± 0.04 | 1.586 ± 0.16 | 5.116 ± 0.00 | 6.711 ± 1.27 |
| 2 hr | 0.22 ± 0.05 | 0.025 ± 0.00 | 0.603 ± 0.05 | 1.716 ± 0.23 | 3.524 ± 0.53 | 4.747 ± 1.78 |
| 4 hr | 0.137 ± 0.02 | 0.021 ± 0.00 | 0.382 ± 0.04 | 1.08 ± 0.16 | 2.604 ± 0.25 | 6.294 ± 1.29 |

| Time | Stomach % dose/g | Kidney % dose/g | Muscle % dose/g | Intestine % dose/g | Bone % dose/g |
|---|---|---|---|---|---|
| 0 min | 0.337 ± 0.00 | 2.66 ± 0.05 | 0.098 ± 0.00 | 0.418 ± 0.03 | 0.244 ± 0.01 |
| 2 min | 0.379 ± 0.02 | 4.145 ± 0.64 | 0.085 ± 0.01 | 0.471 ± 0.00 | 0.234 ± 0.06 |
| 10 min | 0.438 ± 0.03 | 4.251 ± 0.02 | 0.121 ± 0.02 | 0.704 ± 0.08 | 0.3 ± 0.05 |
| 30 min | 0.444 ± 0.09 | 4.095 ± 0.73 | 0.106 ± 0.00 | 1.107 ± 0.31 | 0.324 ± 0.05 |
| 1 hr | 0.625 ± 0.34 | 4.779 ± 0.21 | 0.302 ± 0.39 | 0.896 ± 0.04 | 0.398 ± 0.12 |
| 2 hr | 0.776 ± 0.07 | 5.327 ± 0.52 | 0.111 ± 0.01 | 0.977 ± 0.42 | 0.347 ± 0.01 |
| 4 hr | 0.719 ± 0.18 | 4.282 ± 0.67 | 0.077 ± 0.01 | 0.906 ± 0.24 | 0.264 ± 0.10 |

TABLE 3

Biodistribution of $^{99m}$Tc(N)(PNP2)(DTC)$^+$ in Rats

| Time | Blood % dose/g | Brain % dose/g | Heart % dose/g | Lung % dose/g | Liver % dose/g | Spleen % dose/g |
|---|---|---|---|---|---|---|
| 0 min | 3.220 ± 0.45 | 0.120 ± 0.00 | 1.399 ± 0.08 | 3.568 ± 0.94 | 3.385 ± 0.81 | 2.739 ± 0.07 |
| 2 min | 1.025 ± 0.02 | 0.065 ± 0.01 | 0.728 ± 0.04 | 2.040 ± 0.234 | 7.723 ± 0.20 | 5.018 ± 0.02 |
| 10 min | 0.355 ± 0.03 | 0.040 ± 0.00 | 0.736 ± 0.12 | 1.481 ± 0.10 | 4.686 ± 0.89 | 5.334 ± 0.10 |
| 30 min | 0.333 ± 0.03 | 0.020 ± 0.00 | 0.652 ± 0.19 | 1.015 ± 0.16 | 7.341 ± 0.38 | 5.131 ± 0.59 |
| 1 hr | 0.19 ± 0.01 | 0.025 ± 0.00 | 0.534 ± 0.02 | 1.011 ± 0.01 | 7.436 ± 1.44 | 5.073 ± 0.01 |
| 2 hr | 0.129 ± 0.02 | 0.025 ± 0.00 | 0.511 ± 0.05 | 0.962 ± 0.02 | 4.061 ± 0.64 | 5.507 ± 0.84 |
| 4 hr | 0.087 ± 0.00 | 0.018 ± 0.00 | 0.506 ± 0.04 | 0.670 ± 0.09 | 1.784 ± 0.25 | 5.055 ± 0.02 |

| Time | Stomach % dose/g | Kidney % dose/g | Muscle % dose/g | Intestine % dose/g | Bone % dose/g |
|---|---|---|---|---|---|
| 0 min | 0.752 ± 0.09 | 5.702 ± 0.732 | 0.134 ± 0.01 | 0.906 ± 0.03 | 0.209 ± 0.01 |
| 2 min | 0.0603 ± 0.03 | 4.941 ± 0.60 | 0.077 ± 0.00 | 1.694 ± 0.18 | 0.265 ± 0.04 |
| 10 min | 0.517 ± 0.16 | 6.910 ± 0.081 | 0.064 ± 0.02 | 2.861 ± 0.74 | 0.268 ± 0.10 |
| 30 min | 1.135 ± 0.298 | 7.542 ± 1.410 | 0.103 ± 0.02 | 7.254 ± 0.46 | 0.301 ± 0.03 |
| 1 hr | 0.932 ± 0.12 | 6.713 ± 0.83 | 0.075 ± 0.01 | 7.644 ± 1.01 | 0.294 ± 0.02 |
| 2 hr | 1.701 ± 0.34 | 6.799 ± 1.348 | 0.102 ± 0.02 | 6.442 ± 0.59 | 0.357 ± 0.08 |
| 4 hr | 1.220 ± 0.150 | 7.471 ± 0.03 | 0.08 ± 0.00 | 4.054 ± 0.39 | 0.329 ± 0.01 |

TABLE 4

Biodistribution of $^{99m}$Tc(N)(PNP3)(DTC)$^+$ in Rats

| Time | Blood % dose/g | Brain % dose/g | Heart % dose/g | Lung % dose/g | Liver % dose/g | Spleen % dose/g |
|---|---|---|---|---|---|---|
| 0 min | 1.149 ± 0.04 | 0.096 ± 0.00 | 2.704 ± 0.03 | 2.133 ± 0.03 | 1.5 ± 0.02 | 1.686 ± 0.03 |
| 2 min | 0.421 ± 0.10 | 0.035 ± 0.01 | 3.007 ± 0.16 | 0.995 ± 0.17 | 2.778 ± 0.06 | 1.215 ± 0.1 |
| 10 min | 0.147 ± 0.02 | 0.019 ± 0.00 | 2.506 ± 0.10 | 0.725 ± 0.104 | 1.719 ± 0.14 | 0.856 ± 0.12 |
| 30 min | 0.098 ± 0.01 | 0.012 ± 0.00 | 2.551 ± 0.10 | 0.446 ± 0.00 | 0.732 ± 0.08 | 0.550 ± 0.06 |
| 1 hr | 0.071 ± 0.00 | 0.014 ± 0.00 | 2.155 ± 0.29 | 0.329 ± 0.05 | 0.500 ± 0.01 | 0.238 ± 0.02 |
| 2 hr | 0.049 ± 0.00 | 0.009 ± 0.00 | 2.721 ± 0.06 | 0.312 ± 0.2 | 0.164 ± 0.04 | 0.300 ± 0.05 |
| 4 hr | 0.030 ± 0.00 | 0.009 ± 0.00 | 2.503 ± 0.13 | 0.219 ± 0.01 | 0.155 ± 0.00 | 0.195 ± 0.02 |

TABLE 4-continued

Biodistribution of $^{99m}$Tc(N)(PNP3)(DTC)$^+$ in Rats

| Time | Stomach % dose/g | Kidney % dose/g | Muscle % dose/g | Intestine % dose/g | Bone % dose/g |
|---|---|---|---|---|---|
| 0 min | 1.121 ± 0.01 | 8.289 ± 0.03 | 0.232 ± 0.07 | 2.578 ± 0.350 | 0.198 ± 0.03 |
| 2 min | 0.740 ± 0.02 | 9.676 ± 0.620 | 0.264 ± 0.09 | 4.188 ± 0.60 | 2.242 ± 0.02 |
| 10 min | 0.852 ± 0.118 | 6.559 ± 0.928 | 0.252 ± 0.01 | 10.959 ± 1.64 | 0.204 ± 0.00 |
| 30 min | 1.511 ± 0.39 | 5.354 ± 1.00 | 0.273 ± 0.05 | 10.201 ± 1.28 | 0.230 ± 0.04 |
| 1 hr | 0.892 ± 0.085 | 4.127 ± 0.178 | 0.236 ± 0.04 | 5.447 ± 0.87 | 0.099 ± 0.00 |
| 2 hr | 1.521 ± 0.50 | 3.139 ± 0.20 | 0.268 ± 0.88 | 2.720 ± 0.11 | 0.121 ± 0.00 |
| 4 hr | 0.485 ± 0.07 | 2.536 ± 0.12 | 0.245 ± 0.031 | 1.810 ± 0.716 | 0.079 ± 0.01 |

TABLE 5

Biodistribution of $^{99m}$TcN-DESI in Rats (Group A)

| Time | Blood % dose/g | Brain % dose/g | Heart % dose/g | Lung % dose/g | Liver % dose/g | Spleen % dose/g |
|---|---|---|---|---|---|---|
| 2 min | 0.383 ± 0.287 | 0.082 ± 0.010 | 0.904 ± 0.062 | 0.565 ± 0.074 | 7.259 ± 0.005 | 1.833 ± 0.249 |
| 5 min | 0.349 ± 0.033 | 0.079 ± 0.002 | 0.881 ± 0.071 | 0.425 ± 0.094 | 5.798 ± 0.549 | 1.927 ± 0.155 |
| 10 min | 0.212 ± 0.012 | 0.076 ± 0.003 | 0.894 ± 0.016 | 0.399 ± 0.011 | 4.539 ± 0.286 | 2.139 ± 0.200 |
| 30 min | 0.095 ± 0.024 | 0.070 ± 0.005 | 0.951 ± 0.103 | 0.351 ± 0.085 | 3.069 ± 0.672 | 1.965 ± 0.158 |
| 60 min | 0.069 ± 0.008 | 0.064 ± 0.003 | 0.931 ± 0.025 | 0.224 ± 0.070 | 2.809 ± 0.739 | 1.873 ± 0.667 |
| 120 min | 0.068 ± 0.001 | 0.051 ± 0.001 | 0.806 ± 0.080 | 0.151 ± 0.001 | 1.463 ± 0.186 | 1.453 ± 0.085 |
| 150 min | 0.058 ± 0.008 | 0.034 ± 0.004 | 0.884 ± 0.075 | 0.194 ± 0.002 | 1.375 ± 0.054 | 1.461 ± 0.132 |

| Time | Kidney % dose/g | Muscle % dose/g | Adrenal glands % dose/g | Submaxillary glands % dose/g |
|---|---|---|---|---|
| 2 min | 6.518 ± 0.821 | 0.110 ± 0.004 | 4.227 ± 0.089 | 1.791 ± 0.249 |
| 5 min | 6.193 ± 0.421 | 0.105 ± 0.010 | 3.710 ± 0.682 | 1.721 ± 0.460 |
| 10 min | 6.295 ± 0.329 | 0.096 ± 0.009 | 5.353 ± 0.339 | 1.876 ± 0.030 |
| 30 min | 10.11 ± 1.762 | 0.098 ± 0.021 | 5.153 ± 0.039 | 2.065 ± 0.069 |
| 60 min | 6.227 ± 1.020 | 0.108 ± 0.015 | 4.800 ± 1.737 | 1.491 ± 1.149 |
| 120 min | 5.538 ± 0.607 | 0.397 ± 0.033 | 4.220 ± 0.182 | 1.351 ± 0.037 |
| 150 min | 7.182 ± 0.349 | 0.090 ± 0.009 | 5.013 ± 1.061 | 1.976 ± 0.293 |

TABLE 6

Biodistribution of $^{99m}$TcN-DESI in Rats (Group B)

| Time | Blood % dose/g | Brain % dose/g | Heart % dose/g | Lung % dose/g | Liver % dose/g | Spleen % dose/g |
|---|---|---|---|---|---|---|
| 2 min | 0.467 ± 0.011 | 0.032 ± 0.004 | 0.793 ± 0.037 | 0.488 ± 0.042 | 5.149 ± 0.787 | 1.841 ± 0.197 |
| 5 min | 0.277 ± 0.028 | 0.029 ± 0.003 | 0.819 ± 0.052 | 0.353 ± 0.028 | 6.420 ± 0.378 | 2.032 ± 0.197 |
| 10 min | 0.170 ± 0.020 | 0.018 ± 0.001 | 0.814 ± 0.023 | 0.348 ± 0.003 | 4.732 ± 0.057 | 1.559 ± 0.074 |
| 30 min | 0.169 ± 0.028 | 0.018 ± 0.003 | 0.832 ± 0.170 | 0.27 ± 0.117 | 4.957 ± 0.168 | 1.339 ± 0.380 |
| 60 min | 0.074 ± 0.016 | 0.016 ± 0.002 | 0.693 ± 0.057 | 0.253 ± 0.014 | 2.505 ± 0.113 | 1.403 ± 0.209 |
| 120 min | 0.050 ± 0.007 | 0.004 ± 0.000 | 0.745 ± 0.063 | 0.206 ± 0.048 | 1.159 ± 0.09 | 1.865 ± 0.313 |
| 150 min | 0.050 ± 0.014 | 0.001 ± 0.000 | 0.815 ± 0.070 | 0.163 ± 0.036 | 1.253 ± 0.006 | 1.637 ± 0.147 |

| Time | Kidney % dose/g | Muscle % dose/g | Adrenal glands % dose/g | Submaxillary glands % dose/g |
|---|---|---|---|---|
| 2 min | 5.492 ± 0.602 | 0.103 ± 0.002 | 4.314 ± 0.718 | 1.878 ± 0.09 |
| 5 min | 5.899 ± 1.397 | 0.101 ± 0.014 | 4.480 ± 0.991 | 1.786 ± 0.201 |
| 10 min | 5.192 ± 0.036 | 0.086 ± 0.007 | 4.349 ± 0.164 | 1.669 ± 0.126 |
| 30 min | 7.883 ± 1.689 | 0.091 ± 0.011 | 6.120 ± 2.224 | 1.042 ± 0.123 |
| 60 min | 5.176 ± 0.584 | 0.110 ± 0.024 | 4.321 ± 0.712 | 1.596 ± 0.138 |
| 120 min | 5.737 ± 0.093 | 0.343 ± 0.443 | 4.588 ± 0.985 | 1.641 ± 0.280 |
| 150 min | 5.646 ± 1.192 | 0.096 ± 0.007 | 4.09 ± 0.294 | 1.983 ± 0.339 |

TABLE 7

Regional brain biodistribution of $^{99m}$TcN-DESI in Rate (Group A)

| Time | Cortex % dose/g | Cerebellum % dose/g | Striatum % dose/g | Hypothalamus % dose/g | Medulla % dose/g |
|---|---|---|---|---|---|
| 5 min | 0.029 ± 0.004 | 0.064 ± 0.005 | 0.076 ± 0.025 | 0.325 ± 0.058 | 0.057 ± 0.004 |
| 30 min | 0.021 ± 0.002 | 0.039 ± 0.015 | 0.054 ± 0.017 | 0.408 ± 0.085 | 0.046 ± 0.003 |
| 60 min | 0.021 ± 0.002 | 0.028 ± 0.012 | 0.07 ± 0.019 | 0.364 ± 0.069 | 0.029 ± 0.006 |

TABLE 8

Regional brain biodistribution of $^{99m}$TcN-DESI in Rate (Group B)

| Time | Cortex % dose/g | Cerebellum % dose/g | Striatum % dose/g | Hypothalamus % dose/g | Medulla % dose/g |
|---|---|---|---|---|---|
| 5 min | 0.014 ± 0.004 | 0.048 ± 0.008 | 0.053 ± 0.001 | 0.125 ± 0.029 | 0.038 ± 0.001 |
| 30 min | 0.009 ± 0.002 | 0.035 ± 0.007 | 0.023 ± 0.003 | 0.162 ± 0.106 | 0.027 ± 0.013 |
| 60 min | 0.006 ± 0.000 | 0.031 ± 0.011 | 0.035 ± 0.011 | 0.152 ± 0.033 | 0.016 ± 0.002 |

What is claimed is:

1. A radioactive transition metal nitride heterocomplex comprising a radioactive transition metal nitride and two different ligands coordinated therewith which is represented by the following formula (I):

$$(M\equiv N)XY \qquad (I)$$

wherein a radioactive transition metal M is selected from the group consisting of $^{99m}$Tc, $^{186}$Re, and $^{188}$Re, N is a nitrogen atom, X is a bisphosphine compound represented by the following formula (II):

(II)

wherein,
each of $R^1$, $R^2$, $R^3$ and $R^4$, which may be the same or different, is one member selected from the group consisting of a hydrogen atom, an alkyl group, a substituted alkyl group, an aryl group, and a substituted aryl group,
$R^5$ is a methylene group,
Z is one member selected from the group consisting of a sulfur atom and $NR^6$, wherein,
N is a nitrogen atom and $R^6$ is a hydrogen atom, an alkyl group, a substituted alkyl group, an aryl group, a substituted aryl group, an amino group, an amino acid chain, a biologically active group or a —C(=O)R$^7$ group,
wherein $R^7$ is a hydrogen atom, an alkyl group, a substituted alkyl group, an aryl group, a substituted aryl group, an amino group, an amino acid chain or a biologically active group,
P is a phosphorous atom,
and n is an integer in a range of $1 \leq n \leq 5$
and Y is a bidentate ligand having a combination of two electron-donating atoms which are selected from the group consisting of O, S, and N and may be either charged or not.

2. A radioactive transition metal nitride heterocomplex according to claim 1, wherein said bisphosphine compound X is a bisphosphine compound represented by the following formula (III) or formula (IV):

(III)

wherein,
Ph is a phenyl group and
$R^6$ is a hydrogen atom, an alkyl group, a substituted alkyl group, an aryl group, a substituted aryl group, an amino group, an amino acid chain, a biologically active group, or a —C(=O)R$^7$ group,
wherein $R^7$ is a hydrogen atom, an alkyl group, a substituted alkyl group, an aryl group, a substituted aryl group, an amino group, an amino acid chain or a biologically active group, (IV)

wherein,
X is an integer in a range of $0 \leq X \leq 4$,
W is an integer in a range of $0 \leq W \leq 3$, and
$R^6$ is a hydrogen atom, an alkyl group, a substituted alkyl group, an aryl group, a substituted aryl group, an amino group, an amino acid chain, a biologically active group or a —C(=O)R$^7$ group,
wherein $R^7$ is a hydrogen atom, an alkyl group, a substituted alkyl group, an aryl group, a substituted aryl group, an amino group, an amino acid chain or a biologically active group.

3. A radioactive transition metal nitride heterocomplex according to claim 1, wherein said bisphosphine compound X is selected from the group consisting of bis(diphenylphosphinoethyl)amine, bis(diphenylphosphinoethyl)methylamine, bis(diphenylphosphinoethyl)ethylamine, bis (diphenylphosphinoethyl)propylamine, bis(diphenylphosphinoethyl)butylamine, bis(diphenylphosphinoethyl)acetonylamine and bis(diphenylphosphinoethyl)methoxy ethylamine.

4. A radioactive transition metal nitride heterocomplex according to claim 1, wherein said bis-phosphine compound is selected from the group consisting of $(CH_3O)_2-P-CH_2CH_2-NH-CH_2CH_2-P-(OCH_3)_2$, $(CH_3O)_2-P-CH_2CH_2-N(CH_3)-CH_2CH_2-P-(OCH_3)_2$, $(CH_3O)_2-P-CH_2CH_2-N(CH_2CH_3)-CH_2CH_2-P-(OCH_3)_2$, $(CH_3O)_2-P-CH_2CH_2-N(CH_2CH_2CH_3)-CH_2CH_2-P-(OCH_3)_2$, $[CH_3O(CH_2)_3]_2-P-CH_2CH_2-N(CH_2CH_3)-CH_2CH_2-P-[(CH_2)_3OCH_3]_2$, $[CH_3O(CH_2)_3]_2-P-CH_2CH_2-N(CH_2CH_2CH_3)-CH_2CH_2-P-[(CH_2)_3OCH_3]_2$, $(CH_3CH_2OCH_2CH_2)_2-P-CH_2CH_2-N(CH_2CH_3)-CH_2CH_2-P-(CH_2CH_2OCH_2CH_3)_2$, $(CH_3CH_2OCH_2CH_2)_2-P-CH_2CH_2-N(CH_2CH_2CH_3)-CH_2CH_2-P-(CH_2CH_2OCH_2CH_3)_2$, $[CH_3O(CH_2)_3]_2-P-CH_2CH_2-N(CH_2CH_2OCH_3)-CH_2CH_2-P-[(CH_2)_3\ OCH_3]_2$ and $(CH_3CH_2OCH_2CH_2)_2-P-CH_2CH_2-N(CH_2CH_2OCH_3)-CH_2CH_2-P-(CH_2CH_2OCH_2CH_3)_2$.

5. A radioactive transition metal nitride heterocomplex according to claim 1, wherein said bisphosphine compound X is bis(diphenylphosphinioethyl)sulfide.

6. A radioactive transition metal nitride heterocomplex according to any one of claims 1 or 2 to 5, wherein said bidentate ligand Y is a bidentate ligand having a combination of electron-donating atoms selected from the group consisting of [N⁻, S⁻], [O⁻, S⁻], [S⁻, S⁻], [N⁻, S], [N, S⁻], [O, S⁻], [O, O⁻], [O⁻, N⁻], [N⁻, N⁻], [O⁻, S], [O⁻, O⁻], [O⁻, N], [S, S⁻], [N, N⁻], [O, N⁻], [O, N], [N, N], [S, S], [O, O], [N, S] and [O, S].

7. A radioactive transition metal nitride heterocomplex according to claim 6, wherein said bidentate ligand Y is physiologically active.

8. A radioactive transition metal nitride heterocomplex according to claim 7, wherein said bidentate ligand Y comprises a combination of a physiologically active substance selected from the group consisting of a sugar, an amino acid, a fatty acid, a hormone, a peptide and a receptor-attachable ligand, and said electron-donating atoms.

9. A radioactive transition metal nitride heterocomplex according to claim 6, wherein said bidentate ligand Y is one member selected from the group consisting of 1-thio-β-D-glucose, thiosalicylic acid, cysteine, cysteine ethyl ester, 2-aminoethanethiol, dithiocarbamic acid and derivatives thereof, and dithiocarbazic acid and derivatives thereof.

10. A radioactive transition metal nitride heterocomplex according to claim 9, wherein said dithiocarbamic acid derivatives is one member selected from the group consisting of N-methyl-S-methyl dithiocarbamate, N-diethyl dithiocarbamate, N-ethyl dithiocarbamate and N-ethoxy-N-ethyl dithiocarbamate, or said dithiocarbazic acid derivatives is one member selected from the group consisting of N-ethyl dithiocarbazate and N-methyl-S-methyl dithiocarbazate.

11. A radiopharmaceutical containing, as an active ingredient, a radioactive transition metal nitride heterocomplex comprising a radioactive transition metal nitride and two different ligands coordinated therewith which is represented by the following formula(I):

$$(M\equiv N)XY \tag{I}$$

wherein a radioactive transition metal M is selected from the group consisting of $^{99m}Tc$, $^{186}Re$, and $^{188}Re$, N is a nitrogen atom, X is a bisphosphine compound represented by the following formula (II):

$$R^1\!\!\diagdown_{R^2}\!\!P(R^5_nZ(R^5)_nP\diagup^{R^3}_{\diagdown R^4} \tag{II}$$

wherein, each of $R^1$, $R^2$, $R^3$ and $R^4$, which may be the same or different, is one member selected from the group consisting of a hydrogen atom, an alkyl group, a substituted alkyl group, an aryl group, and a substituted aryl group, $R^5$ is a methylene group, Z is one member selected from the group consisting of a sulfur atom and $NR^6$, wherein, N is a nitrogen atom and $R^6$ is a hydrogen atom, an alkyl group, a substituted alkyl group, an aryl group, a substituted aryl group, an amino group, an amino acid chain, a biologically active group or a —(=O)$R^7$ group, wherein $R^7$ is a hydrogen atom, an alkyl group, a substituted alkyl group, an aryl group, a substituted aryl group, an amino group, an amino acid chain or a biologically active group, P is a phosphorous atom, and n is an integer in a range of $1 \leq n \leq 5$ and Y is a bidentate ligand having a combination of two electron-donating atoms which are selected from the group consisting of O, S, and N and may be either charged or not.

12. A process for producing a radioactive transition metal nitride heterocomplex according to claim 1, which comprises a first step of reacting an oxide of a radioactive transition metal M which is selected from the group consisting of $^{99m}TcO_4^-$, $^{186}ReO_4^-$, and $^{188}ReO_4^-$ with either carbazic acid or its derivative, or hydrazine or its derivative, and a bisphosphine compound of formula II in a solution in the presence or absence of a reducing agent, to obtain an intermediate of radioactive transition metal nitride; and a second step of reacting said intermediate with a bidentate ligand having a combination of two electron-donating atoms selected from the group consisting of O, S and N.

13. A process according to claim 12, wherein said carbazic acid derivative is selected from the group consisting of N-methyl-S-methyl dithiocarbazate, S-methyl dithiocarbazate and N-methyl-S-2-propionic acid dithiocarbazate.

14. A process according to claim 12, wherein said hydrazine derivative is selected from the group consisting of succinic acid hydrazide, acetyl hydrazide and isonicotinic acid hydrazide.

15. A process according to claim 12, wherein said diphosphine compound X is a bisphosphine compound represented by the following formula (II):

(II)

wherein,
each of $R^1$, $R^2$, $R^3$ and $R^4$, which may be the same or different, is one member selected from the group consisting of a hydrogen atom, an alkyl group, a substituted alkyl group, an aryl group, and a substituted aryl group, $R^5$ is a methylene group, Z is one member selected from the group consisting of a sulfur atom and $NR^6$, wherein,
N is a nitrogen atom and $R^6$ is a hydrogen atom, an alkyl group, a substituted alkyl group, an aryl group, a substituted aryl group, an amino group, an amino acid chain, a biologically active group or a —(=O)$R^7$ group,
wherein $R^7$ is a hydrogen atom, an alkyl group, a substituted alkyl group, an aryl group, a substituted aryl group, an amino group, an amino acid chain or a biologically active group, P is a phosphorous atom,
and n is an integer in a range of $1 \leq n \leq 5$.

16. A process according to claim 15, wherein said diphosphine compound X is selected from the group consisting of bis(diphenylphosphinoethyl)amine, bis(diphenylphosphinoethyl)methylamine, bis(diphenylphosphinoethyl)ethylamine, bis(diphenylphosphinoethyl)propylamine, bis(diphenylphosphinoethyl)butylamine, bis(diphenylphosphinoethyl)acetonylamine and bis(diphenylphosphinoethyl)methoxyethylamine.

17. A process according to claim 15, wherein said diphosphine compound X is selected from the group consisting of $(CH_3O)_2$—P—$CH_2CH_2$—NH—$CH_2CH_2$—P—$(OCH_3)_2$, $(CH_3O)_2$—P—$CH_2CH_2$—N($CH_3$)—$CH_2CH_2$—P($OCH_3$)$_2$, $(CH_3O)_2$—P—$CH_2CH_2$—N($CH_2CH_3$)—$CH_2CH_2$—P—$(OCH_3)_2$, $(CH_3O)_2$—P—$CH_2CH_2$—N($CH_2CH_2CH_3$)—$CH_2CH_2$—P—$(OCH_3)_2$, [$CH_3O(CH_2)_3]_2$—P—$CH_2CH_2$—N($CH_2CH_3$)—$CH_2CH_2$—P—$[(CH_2)_3OCH_3]_2$, [$CH_3O(CH_2)_3]_2$—P—$CH_2CH_2$—N($CH_2CH_2CH_3$)—$CH_2CH_2$—P—$[(CH_2)_3OCH_3]_2$, ($CH_3CH_2OCH_2CH_2)_2$—P—$CH_2CH_2$—N($CH_2CH_3$)—$CH_2CH_2$—P—($CH_2CH_2OCH_2CH_3)_2$, ($CH_3CH_2OCH_2CH_2)_2$—P—$CH_2CH_2$—N($CH_2CH_2CH_3$)—$CH_2CH_2$—P—($CH_2CH_2OCH_2CH_3)_2$, [$CH_3O(CH_2)_3]_2$—P—$CH_2CH_2$—N($CH_2CH_2OCH_3$)—$CH_2CH_2$—P—$[(CH_2)_3OCH_3]_2$ and ($CH_3CH_2OCH_2CH_2)_2$—P—$CH_2CH_2$—N($CH_2CH_2OCH_3$)—$CH_2CH_2$—P—($CH_2CH_2OCH_3$)$_2$.

18. A process according to claim 15, wherein said diphosphine compound X is bis(diphenylphosphinoethyl)sulfide.

19. A process according to any one of claims 12 to 18, wherein said bidentate ligand Y is a bidentate ligand having a combination of electron-donating atoms selected from the group consisting of [N$^-$, S$^-$], [O$^-$, S$^-$], [S$^-$, S$^-$], [N$^-$, S], [N, S$^-$], [O, S$^-$], [O, O$^-$], [O$^-$, N$^-$], [N$^-$, N$^-$], [O$^-$, S], [O$^-$, O$^-$], [O$^-$, N], [S, S$^-$], [N, N$^-$], [O, N$^-$], [O, N], [N, N], [S, S], [O, O], [N, S] and [O, S].

20. A process according to claim 19, wherein said bidentate ligand Y is physiologically active.

21. A process according to claim 19, wherein said bidentate ligand Y comprises a combination of a physiologically active substance selected from the group consisting of a sugar, an amino acid, a fatty acid, a hormone, a peptide and a receptor-attachable ligand, and said electron-donating atoms.

22. A process according to claim 19, wherein said bidentate ligand Y is selected from the group consisting of 1-thio-β-D-glucose, thiosalicylic acid, cysteine, cystein ethyl ester, 2-aminoethanethiol, dithiocarbamic acid and derivatives thereof, and dithiocarbazic acid and derivatives thereof.

23. A process according to claim 22, wherein said dithiocarbamic acid derivatives is one member selected from the group consisting of N-methyl-S-methyl dithiocarbamate, N-diethyl dithiocarbamate, N-ethyl dithiocarbamate and N-ethoxy-N-ethyl dithiocarbamate, or said dithiocarbazic acid derivatives is one member selected from the groups consisting of N-ethyl dithiocarbazate and N-methyl-S-methyl dithiocarbazate.

24. A radiopharamceutical containing a radioactive transition metal nitride heterocomplex according to claim 6 as an active ingredient.

25. The radiopharmaceutical of claim 11, wherein said bisphosphine compound X is a bisphosphine compound represented by the following formula (III) or formula (IV):

(III)

wherein,
Ph is a phenyl group and
$R^6$ is a hydrogen atom, an alkyl group, a substituted alkyl group, an aryl group, a substituted aryl group, an amino group, an amino acid chain, a biologically active group, or a —(=O)$R^7$ group,
wherein $R^7$ is a hydrogen atom, an alkyl group, a substituted alkyl group, an aryl group, a substituted aryl group, an amino group, an amino acid chain or a biologically active group, (IV)

wherein,
X is an integer in a range of $0 \leq X \leq 4$,
W is an integer in a range of $0 \leq W \leq 3$, and
$R^6$ is a hydrogen atom, an alkyl group, a substituted alkyl group, an aryl group, a substituted aryl group, an amino group, an amino acid chain, a biologically active group or a —C(=O)$R^7$ group,
wherein $R^7$ is a hydrogen atom, an alkyl group, a substituted alkyl group, an aryl group, a substituted aryl group, an amino group, an amino acid chain or a biologically active group.

26. The radiopharmaceutical of claim 11, wherein said bisphosphine compound X is selected from the group consisting of bis(diphenylphosphinoethyl)amine, bis(diphenylphosphinoethyl)ethylamine, bis(diphenylphosphinoethyl)propylamine, bis(diphenylphosphinoethyl)butylamine, bis(diphenylphosphinoethyl)acetonylamine and bis(diphenylphosphinoethyl)methoxy ethylamine.

27. The radiopharmaceutical of claim 11, wherein said bisphosphine compound is selected from the group consisting of $(CH_3O)_2$—P—$CH_2CH_2$—NH—$CH_2CH_2$—P—$(OCH_3)_2$, $(CH_3O)_2$—P—$CH_2CH_2$—N($CH_3$)—$CH_2CH_2$—P—$(OCH_3)_2$, $(CH_3O)_2$—P—$CH_2CH_2$—N($CH_2CH_3$)—$CH_2CH_2$—P—$(OCH_3)_2$, $(CH_3O)_2$—P—$CH_2CH_2$—N($CH_2CH_2CH_3$)—$CH_2CH_2$—P—$(OCH_3)_2$, $[CH_3O(CH_2)_3]_2$—P—$CH_2CH_2$—N($CH_2CH_3$)—$CH_2CH_2$—P—$[(CH_2)_3OCH_3]_2$, $[CH_3O(CH_2)_3]_2$—P—$CH_2CH_2$—N($CH_2CH_2CH_3$)—$CH_2CH_2$—P—$[(CH_2)_3OCH_3]_2$, $(CH_3CH_2OCH_2CH_2)_2$—P—$CH_2CH_2$—N($CH_2CH_3$)—$CH_2CH_2$—P—$(CH_2CH_2OCH_2CH_3)_2$, $(CH_3CH_2OCH_2CH_2)_2$—P—$CH_2CH_2$—N($CH_2CH_2CH_3$)—$CH_2CH_2$—P—$(CH_2CH_2OCH_2CH_3)_2$, $[CH_3O(CH_2)_3]_2$—P—$CH_2CH_2$—N($CH_2CH_2OCH_3$)—$CH_2CH_2$—P—$[(CH_2)_3OCH_3]_2$ and $(CH_3CH_2OCH_2CH_2)_2$—P—$CH_2CH_2$—N($CH_2CH_2OCH_3$)—$CH_2CH_2$—P—$(CH_2CH_2OCH_2CH_3)_2$.

28. The radiopharmaceutical of claim 11, wherein said bisphosphine compound X is bis(diphenylphosphinoethyl) sulfide.

29. The radiopharmaceutical of any one of claims 11 and 25–28, wherein said bidentate ligand Y is a bidentate ligand having a combination of electron-donating atoms selected from the group consisting of $[N^-, S^-]$, $[O^-, S^-]$, $[S^-, S^-]$, $[N^-, S]$, $[N, S^-]$, $[O, S^-]$, $[O, O^-]$, $[O^-, N^-]$, $[N^-, N^-]$, $[O^-, S]$, $[O^-, O^-]$, $[O^-, N]$, $[S, S^-]$, $[N, N^-]$, $[O, N^-]$, $[O, N]$, $[N, N]$, $[S, S]$, $[O, O]$, $[N, S]$ and $[O, S]$.

30. The radiopharmaceutical of claim 29, wherein said bidentate ligand Y is physiologically active.

31. The radiopharmaceutical of claim 30, wherein said bidentate Y comprises a combination of a physiologically active substance selected from the group consisting of a sugar, an amino acid, a fatty acid, a hormone, a peptide, and a receptor-attachable ligand, and said electron-donating atoms.

32. The radiopharmaceutical of claim 29, wherein said bidentate ligand Y is one member selected from the group consisting of 1-thio-β-D-glucose, thiosalicyclic acid, cysteine, cysteine ethyl ester, 2-aminoethanethiol, dithiocarbamic acid and derivative thereof, and dithiocarbazic acid and derivatives thereof.

33. The radiopharmaceutical of claim 32, wherein said dithiocarbamic acid derivatives is one member selected from the group consisting of N-methyl-S-methyl dithiocarbamate, N-diethyl dithiocarbamate, N-ethyl dithiocarbamate, and N-ethoxy-N-ethyl dithiocarbamate, or said dithiocarbazic acid derivatives is one member selected from the group consisting of N-ethyl dithiocarbazate and N-methyl-S-methyl dithiocarbazate.

\* \* \* \* \*